US010035995B2

(12) United States Patent
Clendennen et al.

(10) Patent No.: US 10,035,995 B2
(45) Date of Patent: Jul. 31, 2018

(54) CALB VARIANTS

(71) Applicants: Eastman Chemical Company, Kingsport, TN (US); North Carolina State University, Raleigh, NC (US)

(72) Inventors: Stephanie Kay Clendennen, Kingsport, TN (US); Yaroslava Georgievna Yingling, Cary, NC (US); Hoshin Kim, Raleigh, NC (US)

(73) Assignees: Eastman Chemical Company, Kingsport, TN (US); North Carolina State University, Raleigh, NC (US)

( * ) Notice: Subject to any disclaimer, the term of this patent is extended or adjusted under 35 U.S.C. 154(b) by 63 days.

(21) Appl. No.: 14/961,237

(22) Filed: Dec. 7, 2015

(65) Prior Publication Data

US 2017/0159034 A1   Jun. 8, 2017

(51) Int. Cl.
| | |
|---|---|
| C12N 9/20 | (2006.01) |
| C12P 21/06 | (2006.01) |
| C12P 21/04 | (2006.01) |
| C12N 15/00 | (2006.01) |
| C12P 13/02 | (2006.01) |
| C12P 7/00 | (2006.01) |
| C07H 21/04 | (2006.01) |
| C12P 7/62 | (2006.01) |
| G06F 19/16 | (2011.01) |
| G06F 19/22 | (2011.01) |
| C12P 21/02 | (2006.01) |

(52) U.S. Cl.
CPC ............... *C12N 9/20* (2013.01); *C12P 7/62* (2013.01); *C12P 13/02* (2013.01); *C12P 21/02* (2013.01); *G06F 19/16* (2013.01); *G06F 19/22* (2013.01); *C12Y 301/01003* (2013.01)

(58) Field of Classification Search
None
See application file for complete search history.

(56) References Cited

U.S. PATENT DOCUMENTS

| | | | |
|---|---|---|---|
| 5,223,409 | A | 6/1993 | Ladner et al. |
| 5,565,335 | A | 10/1996 | Capon et al. |
| 5,643,570 | A | 7/1997 | Theofan et al. |
| 6,277,375 | B1 | 8/2001 | Ward |
| 6,319,691 | B1 | 11/2001 | Pang |
| 8,206,969 | B2 | 6/2012 | Hauer et al. |
| 8,715,970 | B2 | 5/2014 | Hauer et al. |
| 2004/0171154 | A1 | 9/2004 | Storici et al. |
| 2013/0023028 | A1 | 1/2013 | Svendsen et al. |
| 2015/0140588 | A1* | 5/2015 | Besenmatter ............ C12N 9/20 435/19 |

FOREIGN PATENT DOCUMENTS

| | | |
|---|---|---|
| CN | 104745550 | 7/2015 |
| WO | WO9206204 | 4/1992 |
| WO | WO9517413 | 6/1995 |
| WO | WO9522625 | 8/1995 |
| WO | WO2009080676 | 7/2009 |
| WO | WO2011067349 | 6/2011 |
| WO | WO2013010783 | 1/2013 |

OTHER PUBLICATIONS

Schirawski. E6ZUC1—UniProtKB Database. 2014.*
Branden et al. Introduction to Protein Structure, Garland Publishing Inc., New York, p. 247, 1991.*
Partial International Search Report dated Mar. 3, 2017 for PCT application No. PCT/US2016/065255, 11 pages.
"Subname: Full=Uncharacterized protein {ECO:0000313 EMBL:GAC93661.1}" retrieved from EBI accession No. UNITPROT:R9NYC6 Database accession No. R9NYC6 sequence. Jul. 24, 2013, sequence version 1, Konishi et al., "Draft genome sequence of the basidiomycetous yeast-like fungus *Pseudozyma huneiensis* SY62, which produces an abundant amount of the biosurfactant mannosylerythritol lipids".
Anderson et al., "One Biocatalyst—Many Applications: The Use of Candida Antarctica B-Lipase in Organic Synthesis," 1998, Biocatalysis and Biotransformation, 16(3): 181-204, 24 pages.
Berendsen et al., "Molecular dynamics with coupling to an external bath," Oct. 15, 1984, The Journal of Chemical Physics, 81:3684-3290, 7 pages.
Boel et al., "Two different types of intervening sequences in the glucoamylase gene from Aspergillus niger," 1984, The EMBO Journal, 3(7):1581-11585, 5 pages.
Bossa et al., "Molecular dynamics simulation of sperm whale myoglobin: Effects of mutations and trapped CO on the structure and dynamics of cavities," Jul. 2005, Biophysical Journal, vol. 89, 465-474, 10 pages.
Bowie et al., "Identifying determinants of folding and activity for a protein of unknown structure," Apr. 1, 1989, Proc. Natl. Acad. Sci. USA, 86(7): 2152-2156. 5 pages.
Calissano et al., "In vivo site-directed mutagenesis of Neurospora crassa beta-tubulin gene by spheroplasts transformation with oligonucleotides," 1996, Fungal Genetics Newsletter 43: 15-16. 3 pages.
Case, "Amber 12 Reference Manual", 2012, University of California San Francisco, 350 pages.
Chovancova et al., "CAVER 3.0: A tool for the analysis of transport pathways in dynamic protein structures," Oct. 18, 2012, PLOS Computational Biology, 8(10): e1002708, 12 pages.

(Continued)

*Primary Examiner* — Yong D Pak
(74) *Attorney, Agent, or Firm* — Lee & Hayes, PLLC

(57) ABSTRACT

The invention relates to amino acid sequence variants of a lipase with improved activity for catalyzing synthesis reactions and methods of preparing the variants. The methods include predicting amino acid sites for change based on computational models of the protein structure in non-aqueous conditions, and expressing the protein in a prokaryotic host for subsequent purification and use. The enzyme sequence variants described have a three to nine-fold improvement in synthesis activity over the parent protein sequence.

12 Claims, 6 Drawing Sheets

(56) References Cited

OTHER PUBLICATIONS

Emond et al., "New efficient recombinant expression system to engineer Candida antarctica lipase B," Apr. 2010, Applied and Environmental Microbiology, 76(8): 2684-2687. 4 pages.
Gibson et al., "Distal poket resides affect picosecond ligand recombination in myoglobin," Nov. 5, 1992, The Journal of Biological Chemistry, 267(31): 22022-22034, 14 pages.
Hughes et al., "Synthetic resin-bound trunicated Candida antarctica lipase B for production of fatty acid alkyl esters by transesterification of corn and soybean oils with ethanol or butanol," 2012, Journal of Biotechnology, 159: 69-77, 9 pages.
Juhl et al., "Engineering of Candida antarctica lipase B for hydrolysis of bulky carboxylic acid esters," Dec. 2010, Journal of Biotechnology, 150(4): 474-480. 7 pages.
Kim et al., "The relationship between enhanced enzyme activity and structural dynamics in ionic liquids: a combined computational and experimental study," 2014, Phys. Chem. Chem. Phys., 16: 2944-2953, 10 pages.
Kim et al., "The role of hydrogen bonding in water-mediated glucose solubility in ionic liquids," Nov. 26, 2011, Journal of Molecular Liquids, 166: 25-30, 25 pages.
Larsen et al., "Expression of Candida antarctica lipase B in Pichia pastoris and various *Escherichia coli* systems," 2008, Protein Expression and Purification 62: 90-97. 8 pages.
Liu et al., "Rational Design of Pseudozyma antarctica Lipase B yielding a general esterfication catalyst," 2010, ChemBioChem, 11:789-795, 7 pages.
Qian, "Structural redesign of lipase B from candida antarctica by circular permutation and incremental truncation," Journal of Molecular Biology, Oct. 16, 2009, 393(1): 191-201, 18 pages.
Scherer et al., "Replacement of chromosome segments with altered DNA sequences contructed in vitro," Oct. 1979, Proc. Natl. Acad. Sci. USA, 76(10): 4951-4955. 5 pages.
Sindhikara et al., "Bad seeds sprout perilous dynamics: Stochastic thermostat induced trajectory synchonization in biomolecules," 2009, J. Chem. Theory Comput., 5: 1624-1631, 8 pages.
Skjot et al., "Understanding the plasticity of the a/ß hydrolase fold: Lid swapping on the Caandida antarctica Lipase B Results in Chimeras with Interesting Biocatalytic Properties," 2009. ChemBioChem, 10: 520-527, 8 pages.
Syren et al., "Increased activity of enzymatic transacylation of acrylates through rational design of lipases," Aug. 2010, Journal of Molecular Catalysis B: Enzymic, 65(1-4): 3-10. 8 pages.
Tsuge et al., "One step assembly of multiple DNA fragments with a designed order and orientation in Bacillus subtilis plasmid," 2003, Nucleic Acids Research, 31(21): e133. 8 pages.
Uberuaga et al., "Synchronization of trajectories in canonical molecular-dynamics simulations: Observation, explanation and exploitation," Apr. 8, 2004, Journal of Chemical Physics, 120(14): 6363-6374, 12 pages.
Uppenberg et al., "The sequence, crystal structure determination and refinement of two crystal forms of lipase B from Candida antarctica," Apr. 15, 1994, Structure, 2:293-308. 16 pages.
Wang et al., "Automatic atom type and bond type perception in molecular mechanical calculations," 2006, Journal of Graphics and Modelling, 25: 247-260. 14 pages.
Wang et al., "Development and testing of a general Amber force field," 2004, Journal of—Computational Cemistry, 25:1157-1174, 18 pages.
Wang et al., "How well does a restrained electrostatic potential (RESP) model perform in calculating conformational energies of organic and biological molecules?," 2000, Journal of Computational Chemistry, 21(12):1049-1074, 26 pages.
Wu et al., "Laboratory evolution of enantiocomplementary Candida antarctica lipase B mutants with broad substrate scope," 2013, Journal of the American Chemical Society, 135(5): 1872-1881, 10 pages.
Xie et al., "Enhanced enzyme kinetic stability by incereasing rigidity within the active site," Mar. 14, 2014, The Journal of Biological Chemistry, 289(11): 7994-8006, 14 pages.
PCT Search Report and Written Opinion dated Apr. 18, 2017 for PCT Application No. PCT/US16/65255, 24 pages.

\* cited by examiner

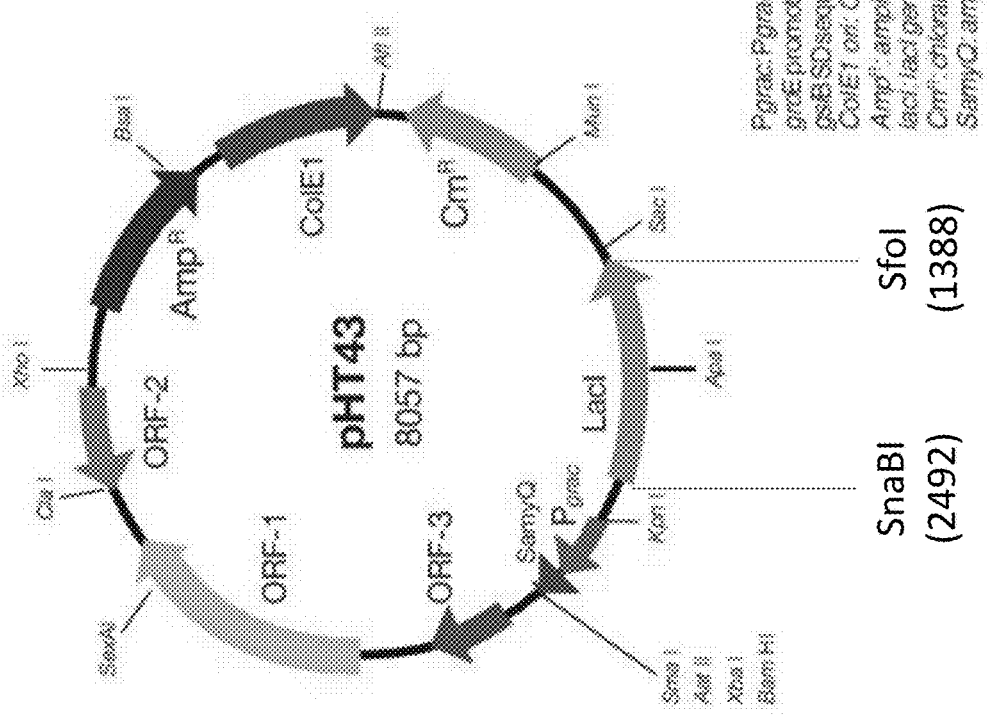

SEQUENCE LISTING

<160> NUMBER OF SEQ ID NOS: 30

<210> SEQ ID NO 1
<211> LENGTH: 951
<212> TYPE: DNA
<213> ORGANISM: Candida Antartica

<400> SEQUENCE: 1
ttgccatctg gttctgatcc agctttctct caaccaaaat ctgtattaga tgctggattg    60

```
acatgccagg gtgcttctcc atcatctgtt tctaagccta ttttattggt acctggtaca    120
ggaactactg gtccacagtc attcgattct aattggatac ccttgtctac tcaattaggt    180
tatacaccat gctggatatc tcctccacca tttatgttaa acgacaccca agtaaatacc    240
gagtacatgg ttaacgcaat aacagcattg tacgccggtt caggaaacaa taagttacca    300
gtattgactt ggtctcaggg tggtttagta gcccaatggg gattgacttt cttcccttca    360
atcagatcaa aagttgacag gttgatggca tttgctccag attacaaagg tacagtcttg    420
gctggtccat tagacgcatt agcagtttct gccccatcag tttggcagca gacaacagga    480
tctgccttaa caactgcctt gagaaacgcc ggtggtttga cccagatcgt tccaactacc    540
aacttgtatt ctgccaccga tgaaatcgtc caaccacaag tttctaactc tccattggat    600
tcttcttact tgtttaatgg taaaaatgtt caagcacaag ccgtctgtgg tcctttgttt    660
gtcattgacc atgcaggttc tttgacctct caatttcctt atgtcgttgg tagatctgct    720
ttgagatcta ctactggtca agcaagatct gctgattatg gtattactga ttgtaatcca    780
ttgcctgcaa atgatttgac tccagaacaa aaagttgcag ctgctgcttt gttggctcca    840
gctgctgctg ctattgttgc tggtccaaag caaaattgtg aaccagattt gatgccttat    900
gctaggcctt tgctgttggg taagagaact tgttctggta ttgttactcc a              951

<210> SEQ ID NO 2
<211> LENGTH: 317
<212> TYPE: PRT
<213> ORGANISM: Candida Antartica

<400> SEQUENCE: 2

Leu Pro Ser Gly Ser Asp Pro Ala Phe Ser Gln Pro Lys Ser Val Leu
1               5                   10                  15

Asp Ala Gly Leu Thr Cys Gln Gly Ala Ser Pro Ser Ser Val Ser Lys
            20                  25                  30

Pro Ile Leu Leu Val Pro Gly Thr Gly Thr Thr Gly Pro Gln Ser Phe
        35                  40                  45

Asp Ser Asn Trp Ile Pro Leu Ser Thr Gln Leu Gly Tyr Thr Pro Cys
    50                  55                  60

Trp Ile Ser Pro Pro Pro Phe Met Leu Asn Asp Thr Gln Val Asn Thr
65                  70                  75                  80

Glu Tyr Met Val Asn Ala Ile Thr Ala Leu Tyr Ala Gly Ser Gly Asn
                85                  90                  95

Asn Lys Leu Pro Val Leu Thr Trp Ser Gln Gly Gly Leu Val Ala Gln
            100                 105                 110

Trp Gly Leu Thr Phe Phe Pro Ser Ile Arg Ser Lys Val Asp Arg Leu
        115                 120                 125

Met Ala Phe Ala Pro Asp Tyr Lys Gly Thr Val Leu Ala Gly Pro Leu
    130                 135                 140

Asp Ala Leu Ala Val Ser Ala Pro Ser Val Trp Gln Gln Thr Thr Gly
145                 150                 155                 160

Ser Ala Leu Thr Thr Ala Leu Arg Asn Ala Gly Gly Leu Thr Gln Ile
                165                 170                 175

Val Pro Thr Thr Asn Leu Tyr Ser Ala Thr Asp Glu Ile Val Gln Pro
            180                 185                 190

Gln Val Ser Asn Ser Pro Leu Asp Ser Ser Tyr Leu Phe Asn Gly Lys
        195                 200                 205

Asn Val Gln Ala Gln Ala Val Cys Gly Pro Leu Phe Val Ile Asp His
    210                 215                 220
```

```
Ala Gly Ser Leu Thr Ser Gln Phe Ser Tyr Val Gly Arg Ser Ala
225                 230                 235                 240

Leu Arg Ser Thr Thr Gly Gln Ala Arg Ser Ala Asp Tyr Gly Ile Thr
                245                 250                 255

Asp Cys Asn Pro Leu Pro Ala Asn Asp Leu Thr Pro Glu Gln Lys Val
            260                 265                 270

Ala Ala Ala Ala Leu Leu Ala Pro Ala Ala Ala Ile Val Ala Gly
        275                 280                 285

Pro Lys Gln Asn Cys Glu Pro Asp Leu Met Pro Tyr Ala Arg Pro Phe
    290                 295                 300

Ala Val Gly Lys Arg Thr Cys Ser Gly Ile Val Thr Pro
305                 310                 315

<210> SEQ ID NO 3
<211> LENGTH: 951
<212> TYPE: DNA
<213> ORGANISM: Artificial
<220> FEATURE:
<223> OTHER INFORMATION: Variant of WT CALB

<400> SEQUENCE: 3
ttgccttcag gttctgaccc agctttctct caaccaaaat ctgtattaga tgctggattg      60
acatgccagg gtgcttctcc atcatctgtt tctaagccta ttttattggt acctggtaca    120
ggaactactg gtccacagtc attcgattct aattggatac ctttgtctac tcaattaggt    180
tatacaccat gctggatatc tcctccacca tttatgttaa acgacaccca agtaaatacc    240
gagtacatgg ttaacgcaat aacagcattg tacgccggtt caggaaacaa taagttacca    300
gtattgactt ggtctcaggg tggtttagta gcccaatggg gattgacttt cttcccttca    360
atcagatcaa aagttgacag gttgatggca tttgctccag attacaaagg tacagtcttg    420
gctggtccat tagacgcatt agcagtttct gccccatcag tttggcagca gacaacagga    480
tctgccttaa caactgcctt gagaaacgcc ggtggtttga cccagatcgt tccaactacc    540
aacttgtatt ctgccaccga tgaaatcgtc aaccacaag tttctaactc tccattggat    600
tcttcttact tgtttaatgg taaaaatgtt caagcacaag ccgtctgtgg tccattgttt    660
gtcatagggc atgctggtac tttgaccctct caatttttctt atgtcgttgg tagatctgct    720
ttgagatcta ctactggtca agcaagatct gctgattatg gtattactga ttgtaatcca    780
ttgcctgcaa atgatttgac tccagaacaa aaagttgcag ctgccgcttt gttggctcca    840
gctgctgctg ctattgttgc tggtccaaag caaaattgtg aaccagattt gatgccttat    900
gctaggcctt ttgctgttgg taagagaact tgttctggta ttgttactcc a            951

<210> SEQ ID NO 4
<211> LENGTH: 317
<212> TYPE: PRT
<213> ORGANISM: Artificial
<220> FEATURE:
<223> OTHER INFORMATION: Variant of CALB

<400> SEQUENCE: 4

Leu Pro Ser Gly Ser Asp Pro Ala Phe Ser Gln Pro Lys Ser Val Leu
1               5                   10                  15

Asp Ala Gly Leu Thr Cys Gln Gly Ala Ser Pro Ser Ser Val Ser Lys
                20                  25                  30

Pro Ile Leu Leu Val Pro Gly Thr Gly Thr Thr Gly Pro Gln Ser Phe
            35                  40                  45
```

```
Asp Ser Asn Trp Ile Pro Leu Ser Thr Gln Leu Gly Tyr Thr Pro Cys
 50                  55                  60

Trp Ile Ser Pro Pro Phe Met Leu Asn Asp Thr Gln Val Asn Thr
 65                  70                  75                  80

Glu Tyr Met Val Asn Ala Ile Thr Ala Leu Tyr Ala Gly Ser Gly Asn
                 85                  90                  95

Asn Lys Leu Pro Val Leu Thr Trp Ser Gln Gly Gly Leu Val Ala Gln
                100                 105                 110

Trp Gly Leu Thr Phe Phe Pro Ser Ile Arg Ser Lys Val Asp Arg Leu
            115                 120                 125

Met Ala Phe Ala Pro Asp Tyr Lys Gly Thr Val Leu Ala Gly Pro Leu
        130                 135                 140

Asp Ala Leu Ala Val Ser Ala Pro Ser Val Trp Gln Gln Thr Thr Gly
145                 150                 155                 160

Ser Ala Leu Thr Thr Ala Leu Arg Asn Ala Gly Gly Leu Thr Gln Ile
                165                 170                 175

Val Pro Thr Thr Asn Leu Tyr Ser Ala Thr Asp Glu Ile Val Gln Pro
                180                 185                 190

Gln Val Ser Asn Ser Pro Leu Asp Ser Ser Tyr Leu Phe Asn Gly Lys
            195                 200                 205

Asn Val Gln Ala Gln Ala Val Cys Gly Pro Leu Phe Val Ile Gly His
        210                 215                 220

Ala Gly Thr Leu Thr Ser Gln Phe Ser Tyr Val Val Gly Arg Ser Ala
225                 230                 235                 240

Leu Arg Ser Thr Thr Gly Gln Ala Arg Ser Ala Asp Tyr Gly Ile Thr
                245                 250                 255

Asp Cys Asn Pro Leu Pro Ala Asn Asp Leu Thr Pro Glu Gln Lys Val
                260                 265                 270

Ala Ala Ala Ala Leu Leu Ala Pro Ala Ala Ala Ile Val Ala Gly
            275                 280                 285

Pro Lys Gln Asn Cys Glu Pro Asp Leu Met Pro Tyr Ala Arg Pro Phe
        290                 295                 300

Ala Val Gly Lys Arg Thr Cys Ser Gly Ile Val Thr Pro
305                 310                 315
```

<210> SEQ ID NO 5
<211> LENGTH: 951
<212> TYPE: DNA
<213> ORGANISM: Artificial
<220> FEATURE:
<223> OTHER INFORMATION: Variant of CALB

<400> SEQUENCE: 5

```
ttgccttcag gttctgaccc agctttctct caaccaaaat ctgtattaga tgctggattg      60
acatgccagg gtgcttctcc atcgtctgtt tctaagccta tttattggt acctggtaca      120
ggaactactg gtccacagtc attcgattct aattggatac ctttgtctac tcaattaggt    180
tatacaccat gctggatatc ccctccacca tttatgttaa acgacaccca agtaaatacc    240
gagtacatgg ttaacgcaat aacagcattg tacgccggtt caggaaacaa taagttacca    300
gtattgactt ggtctcaggg tggtttagta gcccaatggg gattgacttt cttcccttca    360
atcagatcaa agttgacag gttgatggca tttgctccag attataaagg tacagtcttg    420
gctggtccat tagacgcatt agcagtttct gccccatcag tttggcagca gacaacagga    480
tctgccttaa caactgcctt gagaaacgcc ggtggtttga cccagatcgt tccaactacc    540
```

```
aacttgtatt ctgccaccga tgacatcgtc caaccacaag tttctaactc tccattggat    600
tcttcttact tgtttaatgg taaaaatgtt caagcacaag ccgtctgtgg tccattgttt    660
gtcatagggc atgctggtac tttgacctct caattttctt atgtcgttgg tagatctgct    720
ttgagatcta ctactggtca agcaagatct gctgattatg gtattactga ttgtaatcca    780
ttgcctgcaa atgatttgac tccagaacaa aaagttgcag ctgccgcttt gttggctcca    840
gctgctgctg ctattgttgc tggtccaaag caaaattgtg aaccagattt gatgccttat    900
gctaggcctt ttgctgttgg taagagaact tgttctggta ttgttactcc a              951
```

<210> SEQ ID NO 6
<211> LENGTH: 317
<212> TYPE: PRT
<213> ORGANISM: Artificial
<220> FEATURE:
<223> OTHER INFORMATION: Variant of CALB

<400> SEQUENCE: 6

```
Leu Pro Ser Gly Ser Asp Pro Ala Phe Ser Gln Pro Lys Ser Val Leu
1               5                   10                  15

Asp Ala Gly Leu Thr Cys Gln Gly Ala Ser Pro Ser Ser Val Ser Lys
            20                  25                  30

Pro Ile Leu Leu Val Pro Gly Thr Gly Thr Thr Gly Pro Gln Ser Phe
        35                  40                  45

Asp Ser Asn Trp Ile Pro Leu Ser Thr Gln Leu Gly Tyr Thr Pro Cys
    50                  55                  60

Trp Ile Ser Pro Pro Pro Phe Met Leu Asn Asp Thr Gln Val Asn Thr
65                  70                  75                  80

Glu Tyr Met Val Asn Ala Ile Thr Ala Leu Tyr Ala Gly Ser Gly Asn
                85                  90                  95

Asn Lys Leu Pro Val Leu Thr Trp Ser Gln Gly Gly Leu Val Ala Gln
            100                 105                 110

Trp Gly Leu Thr Phe Phe Pro Ser Ile Arg Ser Lys Val Asp Arg Leu
        115                 120                 125

Met Ala Phe Ala Pro Asp Tyr Lys Gly Thr Val Leu Ala Gly Pro Leu
    130                 135                 140

Asp Ala Leu Ala Val Ser Ala Pro Ser Val Trp Gln Gln Thr Thr Gly
145                 150                 155                 160

Ser Ala Leu Thr Thr Ala Leu Arg Asn Ala Gly Gly Leu Thr Gln Ile
                165                 170                 175

Val Pro Thr Thr Asn Leu Tyr Ser Ala Thr Asp Asp Ile Val Gln Pro
            180                 185                 190

Gln Val Ser Asn Ser Pro Leu Asp Ser Ser Tyr Leu Phe Asn Gly Lys
        195                 200                 205

Asn Val Gln Ala Gln Ala Val Cys Gly Pro Leu Phe Val Ile Gly His
    210                 215                 220

Ala Gly Thr Leu Thr Ser Gln Phe Ser Tyr Val Val Gly Arg Ser Ala
225                 230                 235                 240

Leu Arg Ser Thr Thr Gly Gln Ala Arg Ser Ala Asp Tyr Gly Ile Thr
                245                 250                 255

Asp Cys Asn Pro Leu Pro Ala Asn Asp Leu Thr Pro Glu Gln Lys Val
            260                 265                 270

Ala Ala Ala Ala Leu Leu Ala Pro Ala Ala Ala Ile Val Ala Gly
        275                 280                 285
```

Pro Lys Gln Asn Cys Glu Pro Asp Leu Met Pro Tyr Ala Arg Pro Phe
                290                 295                 300

Ala Val Gly Lys Arg Thr Cys Ser Gly Ile Val Thr Pro
305                 310                 315

<210> SEQ ID NO 7
<211> LENGTH: 951
<212> TYPE: DNA
<213> ORGANISM: Artificial
<220> FEATURE:
<223> OTHER INFORMATION: Variant of CALB

<400> SEQUENCE: 7

```
ttgccttcag gttctgaccc agctttctct caaccaaaat ctgtattaga tgctggattg      60
acatgccagg gtgcttctcc atcatctgtt tctaagccta ttttattggt acctggtaca     120
ggaactactg gtccacagtc attcgattct aactggatac ctttgtctac tcaattaggt     180
tatacaccat gctggatatc tcctccacca tttatgttaa cgacaccca agtaaatacc      240
gagtacatgg ttaacgcaat aacagcattg tacgccggtt caggaaacaa taagttacca     300
gtattgactt ggtctcaggg tggtttagta gcccaatggg gattgacttt cttcccttca     360
attagatcaa aagttgacag gttgatggca tttgctccag attacaaagg tacagtcttg     420
actggtccat tagacgcatt agctgttct gccccatcag tttggcagca gacaacagga      480
tctgccttaa caactgcctt gagaaacgcc ggtggtttga cccagatcgt tccaactacc     540
aacttgtatt ctgccaccga tgacatcgtc caaccacaag tttctaactc tccattggat     600
tcttcttact gtttaatgg taaaaatgtt caagcacaag ccgtctgtgg tccattgttt     660
gtcatagggc atgctggtac tttgacctct caattttctt atgtcgttgg tagatctgct     720
ttgagatcta ctactggtca agcaagatct gctgattatg gtattactga ttgtaatcca     780
ttgcctgcaa atgatttgac tccagaacaa aaagttgcag ctgccgcttt gttggctcca     840
gctgctgctg ctattgttgc tggtccaaag caaaattgtg aaccagattt gatgccttat     900
gctaggcctt ttgctgttgg taagagaact tgttctggta ttgttactcc a              951
```

<210> SEQ ID NO 8
<211> LENGTH: 317
<212> TYPE: PRT
<213> ORGANISM: Artificial
<220> FEATURE:
<223> OTHER INFORMATION: Variant of CALB

<400> SEQUENCE: 8

Leu Pro Ser Gly Ser Asp Pro Ala Phe Ser Gln Pro Lys Ser Val Leu
1               5                   10                  15

Asp Ala Gly Leu Thr Cys Gln Gly Ala Ser Pro Ser Ser Val Ser Lys
                20                  25                  30

Pro Ile Leu Leu Val Pro Gly Thr Gly Thr Thr Gly Pro Gln Ser Phe
            35                  40                  45

Asp Ser Asn Trp Ile Pro Leu Ser Thr Gln Leu Gly Tyr Thr Pro Cys
        50                  55                  60

Trp Ile Ser Pro Pro Pro Phe Met Leu Asn Asp Thr Gln Val Asn Thr
65                  70                  75                  80

Glu Tyr Met Val Asn Ala Ile Thr Ala Leu Tyr Ala Gly Ser Gly Asn
                85                  90                  95

Asn Lys Leu Pro Val Leu Thr Trp Ser Gln Gly Gly Leu Val Ala Gln
            100                 105                 110

```
Trp Gly Leu Thr Phe Phe Pro Ser Ile Arg Ser Lys Val Asp Arg Leu
            115                 120                 125
Met Ala Phe Ala Pro Asp Tyr Lys Gly Thr Val Leu Thr Gly Pro Leu
    130                 135                 140
Asp Ala Leu Ala Val Ser Ala Pro Ser Val Trp Gln Gln Thr Thr Gly
145                 150                 155                 160
Ser Ala Leu Thr Thr Ala Leu Arg Asn Ala Gly Leu Thr Gln Ile
                165                 170                 175
Val Pro Thr Thr Asn Leu Tyr Ser Ala Thr Asp Ile Val Gln Pro
            180                 185                 190
Gln Val Ser Asn Ser Pro Leu Asp Ser Ser Tyr Leu Phe Asn Gly Lys
            195                 200                 205
Asn Val Gln Ala Gln Ala Val Cys Gly Pro Leu Phe Val Ile Gly His
            210                 215                 220
Ala Gly Thr Leu Thr Ser Gln Phe Ser Tyr Val Val Gly Arg Ser Ala
225                 230                 235                 240
Leu Arg Ser Thr Thr Gly Gln Ala Arg Ser Ala Asp Tyr Gly Ile Thr
                245                 250                 255
Asp Cys Asn Pro Leu Pro Ala Asn Asp Leu Thr Pro Glu Gln Lys Val
            260                 265                 270
Ala Ala Ala Ala Leu Leu Ala Pro Ala Ala Ala Ile Val Ala Gly
            275                 280                 285
Pro Lys Gln Asn Cys Glu Pro Asp Leu Met Pro Tyr Ala Arg Pro Phe
            290                 295                 300
Ala Val Gly Lys Arg Thr Cys Ser Gly Ile Val Thr Pro
305                 310                 315

<210> SEQ ID NO 9
<211> LENGTH: 951
<212> TYPE: DNA
<213> ORGANISM: Artificial
<220> FEATURE:
<223> OTHER INFORMATION: Variant of CALB

<400> SEQUENCE: 9
ttgccttcag gttctgaccc agctttctct caaccaaaat ctgtattaga tgctggattg      60
acatgccagg gtgcttctcc atcgtctgtt tctaagccta ttttattggt acctggtaca     120
ggaactactg gtccacagtc attcgattct aattggatac ctttgtctac tcaattaggt     180
tatacaccat gctggatatc ccctccacca tttatgttaa cgacaccca agtaaatacc      240 gagtacatgg ttaacgcaat aacagcattg tacgccggtt caggaaacaa taagttacca     300
gtattgactt ggtctcaggg tggtttagta gcccaatggg gattgacttt cttcccttca     360
atcagatcaa aagttgacag gttgatggca tttgctccag attataaagg tacagtcttg     420
acaggtccgt tagacacatt agcagtttct gcaccatcag tttggcagca gacaacagga     480
tctgccttaa caactgcctt gagaaacgcc ggtggtttga cccagatcgt tccaactacc     540
aacttgtatt ctgccaccga tgacatcgtc caaccacaag tttctaactc tccattggat     600
tcttcttact gtttaatgg taaaaatgtt caagcacaag ccgtctgtgg tccattgttt     660
gtcatagggc atgctggtac tttgacctct caattttctt atgtcgttgg tagatctgct     720
ttgagatcta ctactggtca agcaagatct gctgattatg gtattactga ttgtaatcca     780
ttgcctgcaa atgatttgac tccagaacaa aaagttgcag ctgccgcttt gttggctcca     840
gctgctgctg ctattgttgc tggtccaaag caaaattgtg aaccagattt gatgccttat     900
```

```
gctaggcctt tgctgttgg taagagaact tgttctggta tgttactcc a              951
```

<210> SEQ ID NO 10
<211> LENGTH: 317
<212> TYPE: PRT
<213> ORGANISM: Artificial
<220> FEATURE:
<223> OTHER INFORMATION: Variant of CALB

<400> SEQUENCE: 10

```
Leu Pro Ser Gly Ser Asp Pro Ala Phe Ser Gln Pro Lys Ser Val Leu
1               5                   10                  15

Asp Ala Gly Leu Thr Cys Gln Gly Ala Ser Pro Ser Ser Val Ser Lys
            20                  25                  30

Pro Ile Leu Leu Val Pro Gly Thr Gly Thr Thr Gly Pro Gln Ser Phe
        35                  40                  45

Asp Ser Asn Trp Ile Pro Leu Ser Thr Gln Leu Gly Tyr Thr Pro Cys
    50                  55                  60

Trp Ile Ser Pro Pro Pro Phe Met Leu Asn Asp Thr Gln Val Asn Thr
65                  70                  75                  80

Glu Tyr Met Val Asn Ala Ile Thr Ala Leu Tyr Ala Gly Ser Gly Asn
                85                  90                  95

Asn Lys Leu Pro Val Leu Thr Trp Ser Gln Gly Gly Leu Val Ala Gln
            100                 105                 110

Trp Gly Leu Thr Phe Phe Pro Ser Ile Arg Ser Lys Val Asp Arg Leu
        115                 120                 125

Met Ala Phe Ala Pro Asp Tyr Lys Gly Thr Val Leu Thr Gly Pro Leu
    130                 135                 140

Asp Thr Leu Ala Val Ser Ala Pro Ser Val Trp Gln Gln Thr Thr Gly
145                 150                 155                 160

Ser Ala Leu Thr Thr Ala Leu Arg Asn Ala Gly Gly Leu Thr Gln Ile
                165                 170                 175

Val Pro Thr Thr Asn Leu Tyr Ser Ala Thr Asp Asp Ile Val Gln Pro
            180                 185                 190

Gln Val Ser Asn Ser Pro Leu Asp Ser Ser Tyr Leu Phe Asn Gly Lys
        195                 200                 205

Asn Val Gln Ala Gln Ala Val Cys Gly Pro Leu Phe Val Ile Gly His
    210                 215                 220

Ala Gly Thr Leu Thr Ser Gln Phe Ser Tyr Val Val Gly Arg Ser Ala
225                 230                 235                 240

Leu Arg Ser Thr Thr Gly Gln Ala Arg Ser Ala Asp Tyr Gly Ile Thr
                245                 250                 255

Asp Cys Asn Pro Leu Pro Ala Asn Asp Leu Thr Pro Glu Gln Lys Val
            260                 265                 270

Ala Ala Ala Ala Leu Leu Ala Pro Ala Ala Ala Ile Val Ala Gly
        275                 280                 285

Pro Lys Gln Asn Cys Glu Pro Asp Leu Met Pro Tyr Ala Arg Pro Phe
    290                 295                 300

Ala Val Gly Lys Arg Thr Cys Ser Gly Ile Val Thr Pro
305                 310                 315
```

<210> SEQ ID NO 11
<211> LENGTH: 951
<212> TYPE: DNA
<213> ORGANISM: Artificial
<220> FEATURE:
<223> OTHER INFORMATION: Variant of CALB

<400> SEQUENCE: 11

```
ttgccttcag gttctgaccc agctttctct caaccaaaat ctgtattaga tgctggattg      60
acatgccagg gtgcttctcc atcatctgtt tctaagccta ttttattggt acctggtaca     120
ggaactactg gtccacagtc attcgattct aactggatac ctttgtctac tcaattaggt    180
tatacaccat gctggatatc tcctccacca tttatgttaa acgacaccca agtaaatacc    240
gagtacatgg ttaacgcaat aacagcattg tacgccggtt caggaaacaa taagttacca    300
gtattgactt ggtctcaggg tggtttagta gcccaatggg gattgacttt cttcccttca    360
attagatcaa aagttgacag gttgatggca tttgctccag attacaaagg tacagtcttg    420
actggtccat tagacgcatt agctgtttct gccccatcag tttggcagca gacaacagga    480
tctgccttaa caactgcctt gagaaacgcc ggtggtttga cccagatcgt tccaactacc    540
aacttgtatt ctgccaccga tgacgtcgtc caaccacaag tttctaactc tccattggat    600
tcttcttact tgtttaatgg taaaaatgtt caagcacaag ccgtctgtgg tccattgttt    660
gtcataggggc atgctggtac tttgaccctct caattttctt atgtcgttgg tagatctgct    720
ctgagatcta ctactggtca agcaagatct gctgattatg gtattactga ttgtaatcca    780
ttgcctgcaa atgatttgac tccagaacaa aaagttgcag ctgccgcttt gttggctcca    840
gctgctgctg ctattgttgc tggtccaaag caaaattgtg aaccagattt gatgccttat    900
gctaggcctt ttgctgttgg taagagaact tgttctggta ttgttactcc a             951
```

<210> SEQ ID NO 12
<211> LENGTH: 317
<212> TYPE: PRT
<213> ORGANISM: Artificial
<220> FEATURE:
<223> OTHER INFORMATION: Variant of CALB

<400> SEQUENCE: 12

```
Leu Pro Ser Gly Ser Asp Pro Ala Phe Ser Gln Pro Lys Ser Val Leu
1               5                   10                  15

Asp Ala Gly Leu Thr Cys Gln Gly Ala Ser Pro Ser Ser Val Ser Lys
            20                  25                  30

Pro Ile Leu Leu Val Pro Gly Thr Gly Thr Thr Gly Pro Gln Ser Phe
        35                  40                  45

Asp Ser Asn Trp Ile Pro Leu Ser Thr Gln Leu Gly Tyr Thr Pro Cys
    50                  55                  60

Trp Ile Ser Pro Pro Pro Phe Met Leu Asn Asp Thr Gln Val Asn Thr
65                  70                  75                  80

Glu Tyr Met Val Asn Ala Ile Thr Ala Leu Tyr Ala Gly Ser Gly Asn
                85                  90                  95

Asn Lys Leu Pro Val Leu Thr Trp Ser Gln Gly Gly Leu Val Ala Gln
            100                 105                 110

Trp Gly Leu Thr Phe Phe Pro Ser Ile Arg Ser Lys Val Asp Arg Leu
        115                 120                 125

Met Ala Phe Ala Pro Asp Tyr Lys Gly Thr Val Leu Thr Gly Pro Leu
    130                 135                 140

Asp Ala Leu Ala Val Ser Ala Pro Ser Val Trp Gln Gln Thr Thr Gly
145                 150                 155                 160

Ser Ala Leu Thr Thr Ala Leu Arg Asn Ala Gly Gly Leu Thr Gln Ile
                165                 170                 175

Val Pro Thr Thr Asn Leu Tyr Ser Ala Thr Asp Asp Val Val Gln Pro
```

```
              180                 185                 190
Gln Val Ser Asn Ser Pro Leu Asp Ser Ser Tyr Leu Phe Asn Gly Lys
            195                 200                 205

Asn Val Gln Ala Gln Ala Val Cys Gly Pro Leu Phe Val Ile Gly His
        210                 215                 220

Ala Gly Thr Leu Thr Ser Gln Phe Ser Tyr Val Val Gly Arg Ser Ala
225                 230                 235                 240

Leu Arg Ser Thr Thr Gly Gln Ala Arg Ser Ala Asp Tyr Gly Ile Thr
                245                 250                 255

Asp Cys Asn Pro Leu Pro Ala Asn Asp Leu Thr Pro Glu Gln Lys Val
            260                 265                 270

Ala Ala Ala Ala Leu Leu Ala Pro Ala Ala Ala Ile Val Ala Gly
            275                 280                 285

Pro Lys Gln Asn Cys Glu Pro Asp Leu Met Pro Tyr Ala Arg Pro Phe
            290                 295                 300

Ala Val Gly Lys Arg Thr Cys Ser Gly Ile Val Thr Pro
305                 310                 315
```

<210> SEQ ID NO 13
<211> LENGTH: 951
<212> TYPE: DNA
<213> ORGANISM: Artificial
<220> FEATURE:
<223> OTHER INFORMATION: Variant of CALB

<400> SEQUENCE: 13

```
ttgccttcag gttctgaccc ggctttctct caaccaaaat ctgtattaga tgctggattg      60
acatgccagg gtgcttctcc atcgtctgtt tctaagccta ttttattggt acctggtaca     120
ggaactactg gtccacagtc attcgattct aattggatac ctttgtctac tcaattaggt     180
tatacaccat gctggatatc ccctccacca tttatgttaa acgacaccca agtaaatacc     240
gagtacatgg ttaacgcaat aacagcattg tacgccggtt caggaaacaa taagttacca     300
gtattgactt ggtctcaggg tggtttagta gcccaatggg gattgacttt cttcccttca     360
attagatcaa aagttgacag gttgatggca tttgctccag attacaaagg tacagtcttg     420
actggtccat tagacgcatt agcagtttct gccccatcag tttggcagca gacaacagga     480
tctgccctaa caactgcctt gagaaacgcc ggtggtttga cccagatcgt tccaactacc     540
aacttgtatt ctgccaccga tgacatcgtc aaccacaag tttctaactc tccattggat     600
tcttcttact tgtttaatgg taaaaatgtt caagcacaag ccgtctgtgg tccattgttt     660
gtcatagggc atgctggtac tttgacctct caatttctt atgccgttgg tagatccgct     720
ttgagatcta ctactggtca agcaagatct gctgattatg gtattactga ttgtaatcca     780
ttgcctgcaa atgatttgac tccagaacaa aaagttgcag ctgccgcttt gttggctcca     840
gctgctgctg ctattgttgc tggtccaaag caaaattgtg aaccagattt gatgccttat     900
gctaggcctt ttgctgttgg taagagaact tgttctggta ttgttactcc a             951
```

<210> SEQ ID NO 14
<211> LENGTH: 317
<212> TYPE: PRT
<213> ORGANISM: Artificial
<220> FEATURE:
<223> OTHER INFORMATION: Variant of CALB

<400> SEQUENCE: 14

Leu Pro Ser Gly Ser Asp Pro Ala Phe Ser Gln Pro Lys Ser Val Leu

```
1               5                   10                  15
Asp Ala Gly Leu Thr Cys Gln Gly Ala Ser Pro Ser Ser Val Ser Lys
                20                  25                  30
Pro Ile Leu Leu Val Pro Gly Thr Gly Thr Thr Gly Pro Gln Ser Phe
                35                  40                  45
Asp Ser Asn Trp Ile Pro Leu Ser Thr Gln Leu Gly Tyr Thr Pro Cys
        50                  55                  60
Trp Ile Ser Pro Pro Pro Phe Met Leu Asn Asp Thr Gln Val Asn Thr
65                  70                  75                  80
Glu Tyr Met Val Asn Ala Ile Thr Ala Leu Tyr Ala Gly Ser Gly Asn
                85                  90                  95
Asn Lys Leu Pro Val Leu Thr Trp Ser Gln Gly Gly Leu Val Ala Gln
                100                 105                 110
Trp Gly Leu Thr Phe Phe Pro Ser Ile Arg Ser Lys Val Asp Arg Leu
                115                 120                 125
Met Ala Phe Ala Pro Asp Tyr Lys Gly Thr Val Leu Thr Gly Pro Leu
        130                 135                 140
Asp Ala Leu Ala Val Ser Ala Pro Ser Val Trp Gln Gln Thr Thr Gly
145                 150                 155                 160
Ser Ala Leu Thr Thr Ala Leu Arg Asn Ala Gly Gly Leu Thr Gln Ile
                    165                 170                 175
Val Pro Thr Thr Asn Leu Tyr Ser Ala Thr Asp Asp Ile Val Gln Pro
                180                 185                 190
Gln Val Ser Asn Ser Pro Leu Asp Ser Ser Tyr Leu Phe Asn Gly Lys
                195                 200                 205
Asn Val Gln Ala Gln Ala Val Cys Gly Pro Leu Phe Val Ile Gly His
                210                 215                 220
Ala Gly Thr Leu Thr Ser Gln Phe Ser Tyr Ala Val Gly Arg Ser Ala
225                 230                 235                 240
Leu Arg Ser Thr Thr Gly Gln Ala Arg Ser Ala Asp Tyr Gly Ile Thr
                245                 250                 255
Asp Cys Asn Pro Leu Pro Ala Asn Asp Leu Thr Pro Glu Gln Lys Val
                260                 265                 270
Ala Ala Ala Ala Leu Leu Ala Pro Ala Ala Ala Ile Val Ala Gly
                275                 280                 285
Pro Lys Gln Asn Cys Glu Pro Asp Leu Met Pro Tyr Ala Arg Pro Phe
                290                 295                 300
Ala Val Gly Lys Arg Thr Cys Ser Gly Ile Val Thr Pro
305                 310                 315
```

<210> SEQ ID NO 15
<211> LENGTH: 951
<212> TYPE: DNA
<213> ORGANISM: Artificial
<220> FEATURE:
<223> OTHER INFORMATION: Variant of CALB

<400> SEQUENCE: 15

```
ttgccttcag gttctgaccc agctttctct caaccaaaat ctgtattaga tgctggattg    60
acatgccagg gtgcttctcc atcatctgtt tctaagccta ttttattggt acctggtaca   120
ggaactactg gtccacagtc attcgattct aattggatac ctttgtctac tcaattaggt   180
tatacaccat gctggatatc tcctccacca tttatgttaa cgacaccca  agtaaatacc   240
gagtacatgg ttaacgcaat aacagcattg tacgccggtt caggaaacaa taagttacca   300
```

-continued

```
gtattgactt ggtctcaggg tggtttagta gcccaatggg gattgacttt cttcccttca      360
atcagatcaa aagttgacag gttgatggca tttgctccag attataaagg tacagtcttg      420
acgggtccgt tagacacatt agcagtttct gctccatcag tttggcagca gacaacagga      480
tctgccttaa caactgcctt gagaaacgcc ggtggtttga cccagatcgt tccaactacc      540
aacttgtatt ctgccaccga tgacatcgtc aaccacaag tttctaactc tccattggat       600
tcttcttact tgtttaatgg taaaaatgtt caagcacaag ccgtctgtgg tccattgttt      660
gtcataggc atgctggtac tttgacctct caattttctt atgccgttgg tagatccgct       720
ttgagatcta ctactggtca agcaagatct gctgattatg gtattactga ttgtaatcca      780
ttgcctgcaa atgatttgac tccagaacaa aaagttgcag ctgccgcttt gttggctcca      840
gctgctgctg ctattgttgc tggtccaaag caaaattgtg aaccagattt gatgccttat      900
gctaggcctt ttgctgttgg taagagaact tgttctggta ttgttactcc a               951
```

```
<210> SEQ ID NO 16
<211> LENGTH: 317
<212> TYPE: PRT
<213> ORGANISM: Artificial
<220> FEATURE:
<223> OTHER INFORMATION: Variant of CALB

<400> SEQUENCE: 16
```

Leu Pro Ser Gly Ser Asp Pro Ala Phe Ser Gln Pro Lys Ser Val Leu
1               5                   10                  15

Asp Ala Gly Leu Thr Cys Gln Gly Ala Ser Pro Ser Ser Val Ser Lys
            20                  25                  30

Pro Ile Leu Leu Val Pro Gly Thr Gly Thr Thr Gly Pro Gln Ser Phe
        35                  40                  45

Asp Ser Asn Trp Ile Pro Leu Ser Thr Gln Leu Gly Tyr Thr Pro Cys
    50                  55                  60

Trp Ile Ser Pro Pro Pro Phe Met Leu Asn Asp Thr Gln Val Asn Thr
65                  70                  75                  80

Glu Tyr Met Val Asn Ala Ile Thr Ala Leu Tyr Ala Gly Ser Gly Asn
                85                  90                  95

Asn Lys Leu Pro Val Leu Thr Trp Ser Gln Gly Gly Leu Val Ala Gln
            100                 105                 110

Trp Gly Leu Thr Phe Phe Pro Ser Ile Arg Ser Lys Val Asp Arg Leu
        115                 120                 125

Met Ala Phe Ala Pro Asp Tyr Lys Gly Thr Val Leu Thr Gly Pro Leu
    130                 135                 140

Asp Thr Leu Ala Val Ser Ala Pro Ser Val Trp Gln Gln Thr Thr Gly
145                 150                 155                 160

Ser Ala Leu Thr Thr Ala Leu Arg Asn Ala Gly Gly Leu Thr Gln Ile
                165                 170                 175

Val Pro Thr Thr Asn Leu Tyr Ser Ala Thr Asp Asp Ile Val Gln Pro
            180                 185                 190

Gln Val Ser Asn Ser Pro Leu Asp Ser Ser Tyr Leu Phe Asn Gly Lys
        195                 200                 205

Asn Val Gln Ala Gln Ala Val Cys Gly Pro Leu Phe Val Ile Gly His
    210                 215                 220

Ala Gly Thr Leu Thr Ser Gln Phe Ser Tyr Ala Val Gly Arg Ser Ala
225                 230                 235                 240

Leu Arg Ser Thr Thr Gly Gln Ala Arg Ser Ala Asp Tyr Gly Ile Thr
                245                 250                 255

Asp Cys Asn Pro Leu Pro Ala Asn Asp Leu Thr Pro Glu Gln Lys Val
              260                 265                 270

Ala Ala Ala Ala Leu Leu Ala Pro Ala Ala Ala Ile Val Ala Gly
          275                 280                 285

Pro Lys Gln Asn Cys Glu Pro Asp Leu Met Pro Tyr Ala Arg Pro Phe
290                 295                 300

Ala Val Gly Lys Arg Thr Cys Ser Gly Ile Val Thr Pro
305                 310                 315

<210> SEQ ID NO 17
<211> LENGTH: 951
<212> TYPE: DNA
<213> ORGANISM: Artificial
<220> FEATURE:
<223> OTHER INFORMATION: Variant of CALB

<400> SEQUENCE: 17
ttgccttcag gttctgaccc ggctttctct caaccaaaat ctgtattaga tgctggattg      60
acatgccagg gtgcttctcc atcgtctgtt tctaagccta ttttattggt acctggtaca    120
ggaactactg gtccacagtc attcgattct aattggatac ctttgtctac tcaattaggt    180
tatacaccat gctggatatc ccctccacca tttatgttaa cgacaccca gtaaatacc     240
gagtacatgg ttaacgcaat aacagcattg tacgccggtt caggaaacaa taagttacca    300
gtattgactt ggtctcaggg tggtttagta gcccaatggg gattgacttt cttcccttca    360
attagatcaa aagttgacag gttgatggca tttgctccag attacaaagg tacagtcttg    420
accggtccgt tagacacatt agcagtttct gccccatcag tttggcagca gacaacagga    480
tctgccttaa caactgcctt gagaaacgcc ggtggtttga cccagatcgt tccaactacc    540
aacttgtatt ctgccaccga tgacgtcgtc aaccacaag tttctaactc tccattggat    600
tcttcttact tgtttaatgg taaaaatgtt caagcacaag ccgtctgtgg tccattgttt    660
gtcatagggc atgctggtac tttgacctct caattttctt atgtcgttgg tagatctgct    720
ctgagatcta ctactggtca agcaagatct gctgattatg gtattactga ttgtaatccg    780
ttgcctgcaa atgatttgac tccagaacaa aaagttgcag ctgccgcttt gttggctcca    840
gctgctgctg ctattgttgc tggtccaaag caaaattgtg aaccagattt gatgccttat    900
gctaggcctt ttgctgttgg taagagaact tgttctggta ttgttactcc a            951

<210> SEQ ID NO 18
<211> LENGTH: 317
<212> TYPE: PRT
<213> ORGANISM: Artificial
<220> FEATURE:
<223> OTHER INFORMATION: Variant of CALB

<400> SEQUENCE: 18

Leu Pro Ser Gly Ser Asp Pro Ala Phe Ser Gln Pro Lys Ser Val Leu
1               5                   10                  15

Asp Ala Gly Leu Thr Cys Gln Gly Ala Ser Pro Ser Ser Val Ser Lys
            20                  25                  30

Pro Ile Leu Leu Val Pro Gly Thr Gly Thr Gly Pro Gln Ser Phe
        35                  40                  45

Asp Ser Asn Trp Ile Pro Leu Ser Thr Gln Leu Gly Tyr Thr Pro Cys
    50                  55                  60

Trp Ile Ser Pro Pro Pro Phe Met Leu Asn Asp Thr Gln Val Asn Thr
65                  70                  75                  80

Glu Tyr Met Val Asn Ala Ile Thr Ala Leu Tyr Ala Gly Ser Gly Asn
                    85                  90                  95

Asn Lys Leu Pro Val Leu Thr Trp Ser Gln Gly Gly Leu Val Ala Gln
            100                 105                 110

Trp Gly Leu Thr Phe Phe Pro Ser Ile Arg Ser Lys Val Asp Arg Leu
        115                 120                 125

Met Ala Phe Ala Pro Asp Tyr Lys Gly Thr Val Leu Thr Gly Pro Leu
130                 135                 140

Asp Thr Leu Ala Val Ser Ala Pro Ser Val Trp Gln Gln Thr Thr Gly
145                 150                 155                 160

Ser Ala Leu Thr Thr Ala Leu Arg Asn Ala Gly Gly Leu Thr Gln Ile
                165                 170                 175

Val Pro Thr Thr Asn Leu Tyr Ser Ala Thr Asp Asp Val Val Gln Pro
            180                 185                 190

Gln Val Ser Asn Ser Pro Leu Asp Ser Ser Tyr Leu Phe Asn Gly Lys
        195                 200                 205

Asn Val Gln Ala Gln Ala Val Cys Gly Pro Leu Phe Val Ile Gly His
210                 215                 220

Ala Gly Thr Leu Thr Ser Gln Phe Ser Tyr Val Val Gly Arg Ser Ala
225                 230                 235                 240

Leu Arg Ser Thr Thr Gly Gln Ala Arg Ser Ala Asp Tyr Gly Ile Thr
                245                 250                 255

Asp Cys Asn Pro Leu Pro Ala Asn Asp Leu Thr Pro Glu Gln Lys Val
            260                 265                 270

Ala Ala Ala Ala Leu Leu Ala Pro Ala Ala Ala Ile Val Ala Gly
        275                 280                 285

Pro Lys Gln Asn Cys Glu Pro Asp Leu Met Pro Tyr Ala Arg Pro Phe
290                 295                 300

Ala Val Gly Lys Arg Thr Cys Ser Gly Ile Val Thr Pro
305                 310                 315

<210> SEQ ID NO 19
<211> LENGTH: 951
<212> TYPE: DNA
<213> ORGANISM: Artificial
<220> FEATURE:
<223> OTHER INFORMATION: Variant of CALB

<400> SEQUENCE: 19
ttgccttcag gttctgaccc ggctttctct caaccaaaat ctgtattaga tgctggattg      60
acatgccagg gtgcttctcc atcgtctgtt tctaagccta tttattggt acctggtaca     120 ggaactactg gtccacagtc attcgattct aattggatac ctttgtctac tcaattaggt    180
tatacaccat gctggatatc ccctccacca tttatgttaa cgacaccca agtaaatacc     240 gagtacatgg ttaacgcaat aacagcattg tacgccggtt caggaaacaa taagttacca    300
gtattgactt ggtctcaggg tggtttagta gcccaatggg gattgacttt cttcccttca    360
attagatcaa aagttgacag gttgatggca tttgctccag attacaaagg tacagtcttg    420
actggtccat agacgcatt agcagtttct gccccatcag tttggcagca gacaacagga    480
tctgccctaa caactgcctt gagaaacgcc ggtggtttga cccagatcgt tccaactacc    540
aacttgtatt ctgccaccga tgacgtcgtc caaccacaag tttctaactc tccattggat    600
tcttcttact gtttaatgg taaaaatgtt caagcacaag ccgtctgtgg tccattgttt    660 gtcataggc atgctggtac tttgacctct caatttttctt atgccgttgg tagatccgct    720

```
ttgagatcta ctactggtca agcaagatct gctgattatg gtattactga ttgtaatcca    780
ttgcctgcaa atgatttgac tccagaacaa aaagttgcag ctgccgcttt gttggctcca    840
gctgctgctg ctattgttgc tggtccaaag caaaattgtg aaccagattt gatgccttat    900
gctaggcctt ttgctgttgg taagagaact tgttctggta tgttactcc a              951
```

<210> SEQ ID NO 20
<211> LENGTH: 317
<212> TYPE: PRT
<213> ORGANISM: Artificial
<220> FEATURE:
<223> OTHER INFORMATION: Variant of CALB

<400> SEQUENCE: 20

```
Leu Pro Ser Gly Ser Asp Pro Ala Phe Ser Gln Pro Lys Ser Val Leu
1               5                   10                  15

Asp Ala Gly Leu Thr Cys Gln Gly Ala Ser Pro Ser Ser Val Ser Lys
            20                  25                  30

Pro Ile Leu Leu Val Pro Gly Thr Gly Thr Thr Gly Pro Gln Ser Phe
        35                  40                  45

Asp Ser Asn Trp Ile Pro Leu Ser Thr Gln Leu Gly Tyr Thr Pro Cys
    50                  55                  60

Trp Ile Ser Pro Pro Pro Phe Met Leu Asn Asp Thr Gln Val Asn Thr
65                  70                  75                  80

Glu Tyr Met Val Asn Ala Ile Thr Ala Leu Tyr Ala Gly Ser Gly Asn
                85                  90                  95

Asn Lys Leu Pro Val Leu Thr Trp Ser Gln Gly Gly Leu Val Ala Gln
            100                 105                 110

Trp Gly Leu Thr Phe Phe Pro Ser Ile Arg Ser Lys Val Asp Arg Leu
        115                 120                 125

Met Ala Phe Ala Pro Asp Tyr Lys Gly Thr Val Leu Thr Gly Pro Leu
    130                 135                 140

Asp Ala Leu Ala Val Ser Ala Pro Ser Val Trp Gln Gln Thr Thr Gly
145                 150                 155                 160

Ser Ala Leu Thr Thr Ala Leu Arg Asn Ala Gly Gly Leu Thr Gln Ile
                165                 170                 175

Val Pro Thr Thr Asn Leu Tyr Ser Ala Thr Asp Asp Val Val Gln Pro
            180                 185                 190

Gln Val Ser Asn Ser Pro Leu Asp Ser Ser Tyr Leu Phe Asn Gly Lys
        195                 200                 205

Asn Val Gln Ala Gln Ala Val Cys Gly Pro Leu Phe Val Ile Gly His
    210                 215                 220

Ala Gly Thr Leu Thr Ser Gln Phe Ser Tyr Ala Val Gly Arg Ser Ala
225                 230                 235                 240

Leu Arg Ser Thr Thr Gly Gln Ala Arg Ser Ala Asp Tyr Gly Ile Thr
                245                 250                 255

Asp Cys Asn Pro Leu Pro Ala Asn Asp Leu Thr Pro Glu Gln Lys Val
            260                 265                 270

Ala Ala Ala Ala Leu Leu Ala Pro Ala Ala Ala Ile Val Ala Gly
        275                 280                 285

Pro Lys Gln Asn Cys Glu Pro Asp Leu Met Pro Tyr Ala Arg Pro Phe
    290                 295                 300

Ala Val Gly Lys Arg Thr Cys Ser Gly Ile Val Thr Pro
305                 310                 315
```

<210> SEQ ID NO 21
<211> LENGTH: 951
<212> TYPE: DNA
<213> ORGANISM: Artificial
<220> FEATURE:
<223> OTHER INFORMATION: Variant of CALB

<400> SEQUENCE: 21

```
ttgccttcag gttctgaccc ggctttctct caaccaaaat ctgtattaga tgctggattg      60
acatgccagg gtgcttctcc atcgtctgtt tctaagccta tttttattgg acctggtaca     120
ggaactactg gtccacagtc attcgattct aattggatac ctttgtctac tcaattaggt     180
tatacaccat gctggatatc ccctccacca tttatgttaa acgacaccca agtaaatacc     240
gagtacatgg ttaacgcaat aacagcattg tacgccggtt caggaaacaa taagttacca     300
gtattgactt ggtctcaggg tggtttagta gcccaatggg gattgacttt cttcccttca     360
attagatcaa aagttgacag gttgatggca tttgctccag attacaaagg tacagtcttg     420
actggtccgt tagacacatt agcagtttct gccccatcag tttggcagca gacaacagga     480
tctgccttaa caactgcctt gagaaacgcc ggtggtttga cccagatcgt tccaactacc     540
aacttgtatt ctgccaccga tgacgtcgtc caacccacaa tttctaactc tccattggat     600
tcttcttact tgtttaatgg taaaaatgtt caagcacaag ccgtctgtgg tccattgttt     660
gtcatagggc atgctggtac tttgacctct caatttttctt atgccgttgg tagatccgct     720
ttgagatcta ctactggtca agcaagatct gctgattatg gtattactga ttgtaatcca     780
ttgcctgcaa atgatttgac tccagaacaa aaagttgcag ctgccgcttt gttggctcca     840
gctgctgctg ctattgttgc tggtccaaag caaaattgtg aaccagattt gatgccttat     900
gctaggcctt ttgctgttgg taagagaact tgttctggta tgttactcc a                951
```

<210> SEQ ID NO 22
<211> LENGTH: 317
<212> TYPE: PRT
<213> ORGANISM: Artificial
<220> FEATURE:
<223> OTHER INFORMATION: Variant of CALB

<400> SEQUENCE: 22

```
Leu Pro Ser Gly Ser Asp Pro Ala Phe Ser Gln Pro Lys Ser Val Leu
1               5                   10                  15

Asp Ala Gly Leu Thr Cys Gln Gly Ala Ser Pro Ser Ser Val Ser Lys
                20                  25                  30

Pro Ile Leu Leu Val Pro Gly Thr Gly Thr Thr Gly Pro Gln Ser Phe
            35                  40                  45

Asp Ser Asn Trp Ile Pro Leu Ser Thr Gln Leu Gly Tyr Thr Pro Cys
        50                  55                  60

Trp Ile Ser Pro Pro Pro Phe Met Leu Asn Asp Thr Gln Val Asn Thr
65                  70                  75                  80

Glu Tyr Met Val Asn Ala Ile Thr Ala Leu Tyr Ala Gly Ser Gly Asn
                85                  90                  95

Asn Lys Leu Pro Val Leu Thr Trp Ser Gln Gly Gly Leu Val Ala Gln
            100                 105                 110

Trp Gly Leu Thr Phe Phe Pro Ser Ile Arg Ser Lys Val Asp Arg Leu
        115                 120                 125

Met Ala Phe Ala Pro Asp Tyr Lys Gly Thr Val Leu Thr Gly Pro Leu
    130                 135                 140
```

-continued

Asp Thr Leu Ala Val Ser Ala Pro Ser Val Trp Gln Gln Thr Thr Gly
145                 150                 155                 160

Ser Ala Leu Thr Thr Ala Leu Arg Asn Ala Gly Gly Leu Thr Gln Ile
                165                 170                 175

Val Pro Thr Thr Asn Leu Tyr Ser Ala Thr Asp Asp Val Val Gln Pro
            180                 185                 190

Gln Val Ser Asn Ser Pro Leu Asp Ser Ser Tyr Leu Phe Asn Gly Lys
        195                 200                 205

Asn Val Gln Ala Gln Ala Val Cys Gly Pro Leu Phe Val Ile Gly His
    210                 215                 220

Ala Gly Thr Leu Thr Ser Gln Phe Ser Tyr Ala Val Gly Arg Ser Ala
225                 230                 235                 240

Leu Arg Ser Thr Thr Gly Gln Ala Arg Ser Ala Asp Tyr Gly Ile Thr
                245                 250                 255

Asp Cys Asn Pro Leu Pro Ala Asn Asp Leu Thr Pro Glu Gln Lys Val
            260                 265                 270

Ala Ala Ala Ala Leu Leu Ala Pro Ala Ala Ala Ile Val Ala Gly
        275                 280                 285

Pro Lys Gln Asn Cys Glu Pro Asp Leu Met Pro Tyr Ala Arg Pro Phe
290                 295                 300

Ala Val Gly Lys Arg Thr Cys Ser Gly Ile Val Thr Pro
305                 310                 315

<210> SEQ ID NO 23
<211> LENGTH: 29
<212> TYPE: DNA
<213> ORGANISM: Artificial
<220> FEATURE:
<223> OTHER INFORMATION: Primer

<400> SEQUENCE: 23
gcttggtacc agctattgta acataatcg                                    29

<210> SEQ ID NO 24
<211> LENGTH: 26
<212> TYPE: DNA
<213> ORGANISM: Artificial
<220> FEATURE:
<223> OTHER INFORMATION: Primer

<400> SEQUENCE: 24
cagacaaaga tctccatgga cgcgtg                                       26

<210> SEQ ID NO 25
<211> LENGTH: 42
<212> TYPE: DNA
<213> ORGANISM: Artificial
<220> FEATURE:
<223> OTHER INFORMATION: Primer

<400> SEQUENCE: 25
ggtaagagaa cttgttctgg tattgttact ccataataac cc                     42

<210> SEQ ID NO 26
<211> LENGTH: 40
<212> TYPE: DNA
<213> ORGANISM: Artificial
<220> FEATURE:
<223> OTHER INFORMATION: Primer

<400> SEQUENCE: 26
cagcgtgcac ataagcacaa gtctgaacga aactgtccgc                                40

<210> SEQ ID NO 27
<211> LENGTH: 40
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (17)..(19)
<223> OTHER INFORMATION: n is a, c, g, or t

<400> SEQUENCE: 27
gtattctgcc accgatnnna tcgtccaacc acaagtttct                                40

<210> SEQ ID NO 28
<211> LENGTH: 37
<212> TYPE: DNA
<213> ORGANISM: Artificial
<220> FEATURE:
<223> OTHER INFORMATION: Primer

<400> SEQUENCE: 28
ccattaaaca agtaagaaga atccaatgga gagttag                                   37

<210> SEQ ID NO 29
<211> LENGTH: 317
<212> TYPE: PRT
<213> ORGANISM: Artificial
<220> FEATURE:
<223> OTHER INFORMATION: Variant of CALB

<400> SEQUENCE: 29

Leu Pro Ser Gly Ser Asp Pro Ala Phe Ser Gln Pro Lys Ser Val Leu
1               5                   10                  15

Asp Ala Gly Leu Thr Cys Gln Gly Ala Ser Pro Ser Ser Val Ser Lys
                20                  25                  30

Pro Ile Leu Leu Val Pro Gly Thr Gly Thr Thr Gly Pro Gln Ser Phe
            35                  40                  45

Asp Ser Asn Trp Ile Pro Leu Ser Thr Gln Leu Gly Tyr Thr Pro Cys
    50                  55                  60

Trp Ile Ser Pro Pro Pro Phe Met Leu Asn Asp Thr Gln Val Asn Thr
65                  70                  75                  80

Glu Tyr Met Val Asn Ala Ile Thr Ala Leu Tyr Ala Gly Ser Gly Asn
                85                  90                  95

Asn Lys Leu Pro Val Leu Thr Trp Ser Gln Gly Gly Leu Val Ala Gln
            100                 105                 110

Trp Gly Leu Thr Phe Phe Pro Ser Ile Arg Ser Lys Val Asp Arg Leu
        115                 120                 125

Met Ala Phe Ala Pro Asp Tyr Lys Gly Thr Val Leu Ala Gly Pro Leu
    130                 135                 140

Asp Ala Leu Ala Val Ser Ala Pro Ser Val Trp Gln Gln Thr Thr Gly
145                 150                 155                 160

Ser Ala Leu Thr Thr Ala Leu Arg Asn Ala Gly Gly Leu Thr Gln Ile
                165                 170                 175

Val Pro Thr Thr Asn Leu Tyr Ser Ala Thr Asp Glu Ile Val Gln Pro
            180                 185                 190

Gln Val Ser Asn Ser Pro Leu Asp Ser Ser Tyr Leu Phe Asn Gly Lys
        195                 200                 205

```
Asn Val Gln Ala Gln Ala Val Cys Gly Pro Leu Phe Val Ile Gly His
    210                 215                 220

Ala Gly Ser Leu Thr Ser Gln Phe Ser Tyr Val Val Gly Arg Ser Ala
225                 230                 235                 240

Leu Arg Ser Thr Thr Gly Gln Ala Arg Ser Ala Asp Tyr Gly Ile Thr
                    245                 250                 255

Asp Cys Asn Pro Leu Pro Ala Asn Asp Leu Thr Pro Glu Gln Lys Val
                260                 265                 270

Ala Ala Ala Ala Leu Leu Ala Pro Ala Ala Ala Ile Val Ala Gly
                275                 280                 285

Pro Lys Gln Asn Cys Glu Pro Asp Leu Met Pro Tyr Ala Arg Pro Phe
290                 295                 300

Ala Val Gly Lys Arg Thr Cys Ser Gly Ile Val Thr Pro
305                 310                 315

<210> SEQ ID NO 30
<211> LENGTH: 317
<212> TYPE: PRT
<213> ORGANISM: Artificial
<220> FEATURE:
<223> OTHER INFORMATION: Variant of CALB

<400> SEQUENCE: 30

Leu Pro Ser Gly Ser Asp Pro Ala Phe Ser Gln Pro Lys Ser Val Leu
1               5                   10                  15

Asp Ala Gly Leu Thr Cys Gln Gly Ala Ser Pro Ser Ser Val Ser Lys
                20                  25                  30

Pro Ile Leu Leu Val Pro Gly Thr Gly Thr Thr Gly Pro Gln Ser Phe
            35                  40                  45

Asp Ser Asn Trp Ile Pro Leu Ser Thr Gln Leu Gly Tyr Thr Pro Cys
    50                  55                  60

Trp Ile Ser Pro Pro Pro Phe Met Leu Asn Asp Thr Gln Val Asn Thr
65                  70                  75                  80

Glu Tyr Met Val Asn Ala Ile Thr Ala Leu Tyr Ala Gly Ser Gly Asn
                85                  90                  95

Asn Lys Leu Pro Val Leu Thr Trp Ser Gln Gly Gly Leu Val Ala Gln
                100                 105                 110

Trp Gly Leu Thr Phe Phe Pro Ser Ile Arg Ser Lys Val Asp Arg Leu
            115                 120                 125

Met Ala Phe Ala Pro Asp Tyr Lys Gly Thr Val Leu Ala Gly Pro Leu
130                 135                 140

Asp Ala Leu Ala Val Ser Ala Pro Ser Val Trp Gln Gln Thr Thr Gly
145                 150                 155                 160

Ser Ala Leu Thr Thr Ala Leu Arg Asn Ala Gly Gly Leu Thr Gln Ile
                165                 170                 175

Val Pro Thr Thr Asn Leu Tyr Ser Ala Thr Asp Glu Ile Val Gln Pro
            180                 185                 190

Gln Val Ser Asn Ser Pro Leu Asp Ser Ser Tyr Leu Phe Asn Gly Lys
            195                 200                 205

Asn Val Gln Ala Gln Ala Val Cys Gly Pro Leu Phe Val Ile Asp His
    210                 215                 220

Ala Gly Thr Leu Thr Ser Gln Phe Ser Tyr Val Val Gly Arg Ser Ala
225                 230                 235                 240

Leu Arg Ser Thr Thr Gly Gln Ala Arg Ser Ala Asp Tyr Gly Ile Thr
                    245                 250                 255
```

```
Asp Cys Asn Pro Leu Pro Ala Asn Asp Leu Thr Pro Glu Gln Lys Val
            260                 265                 270

Ala Ala Ala Ala Leu Leu Ala Pro Ala Ala Ala Ile Val Ala Gly
        275                 280             285

Pro Lys Gln Asn Cys Glu Pro Asp Leu Met Pro Tyr Ala Arg Pro Phe
    290                 295                 300

Ala Val Gly Lys Arg Thr Cys Ser Gly Ile Val Thr Pro
305                 310                 315
```

CALB VARIANTS

SEQUENCE LISTING INFORMATION

A computer readable textfile, entitled CALB Variants "E023-0054US-Sequence Listing.txt," created on or about Nov. 10, 2015, with a file size of about 52 KB, contains the sequence listing for this application and is hereby incorporated by reference in its entirety.

FIELD

The present disclosure relates to variants of *Candida antarctica* lipase B (CALB) having improved lipase activity as compared to wild type CALB, methods of identifying the variants, and methods of using the variants.

BACKGROUND

The *Candida antarctica* lipase B (CALB) is able to catalyze synthesis reactions, with esterification reactions catalyzed by CALB being particularly well-studied. While CALB is able to react with a wide variety of alcohol substrates to form esters, it is more limited in the type of acid substrate it recognizes, with preference for straight-chain fatty acids.

Eukaryotic hosts like fungi and the yeasts *Saccharomyces cerevisiae*, *Yarrowia lipolytica* and *Pichia pastoris* have been engineered to produce a secreted form of CALB. CALB is also supplied commercially, expressed and secreted in a recombinant fungal or yeast host (Novozymes and cLecta product data sheets). However, low transformation efficiency and long growth periods make these eukaryotic systems difficult to use for high-throughput screening of large numbers of enzyme variants. Typically, DNA constructs must pass or "shuttle" through an *E. coli* or other bacterial host prior to introduction into the eukaryotic host, and the cells must be grown for several days, often in the presence of an inducer to stimulate expression. In addition, a generally useful secretion system for extracellular lipase expression in yeast is lacking, and efficient recovery of the recombinant lipase requires the lipase to be active outside the host cell in a cell-free system. The expression of the eukaryotic CALB enzyme has been accomplished in the common bacterial (prokaryotic) host *E. coli*, but not secretion, and so a subsequent cell-lysis step is required to liberate the lipase for characterization. Frequently only the hydrolytic activity of these recombinant lipases was confirmed, but not synthesis activity. A recent publication summarizes the difficulty of expressing CALB in a heterologous host, especially a bacterial host (Larsen et al., 2008). The authors hypothesize that incorrect protein folding in *E. coli* is a limitation in expression of CALB in this bacterial host.

A CALB variant with improved activity for synthesis reactions would improve the efficiency of esterification, amidation and transesterification reactions and permit the economic manufacture of compounds using an enzyme catalyst. A CALB variant with improved activity for synthesis reactions would also permit the use of an enzyme catalyst to synthesize derivatives of hindered substrates. While some CALB variants having improved hydrolytic activity have been prepared, these variants are irrelevant to improving synthetic activity, which occurs in the absence of water. In order to identify amino acid changes in the native CALB sequence to target for change and to measure and understand the impact of amino acid changes on structure and function of the enzyme, it is also necessary to devise methods for predicting the protein structure in synthesis conditions, that is in the absence of water, and also to devise a method for expressing the enzyme variants and isolating them in a form suitable for synthesis reactions.

SUMMARY

The present disclosure provides CALB variants having improved synthesis activity. Moreover, the present disclosure provides a new bacterial expression system using *Bacillus subtilis* (Bsub) for expressing CALB. The bacterial expression system is suitable for high-throughput screening of enzyme variants. Additionally, the present invention provides an improved method for molecular dynamic simulation analysis to accurately determine amino acid residues for alteration to obtain CALB variants with improved functional activity.

The present disclosure provides *Candida antarctica* lipase B (CALB) variants having about two fold to about fifteen fold improved synthetic activity as compared to a wild type (WT) CALB. In embodiments, the CALB variant has an amino acid sequence having one or more modifications and the one or more modifications can be at position 141, 146, 188, 189, 223, 227, or 235 of SEQ ID NO: 2. In other embodiments, the CALB variant has two to seven amino acid substitutions and the amino acid substitutions can be at position 141, 146, 188, 189, 223, 227, or 235 of SEQ ID NO: 2. In further embodiments, the amino acid substitutions for the CALB variants include one or more of the following: A141T, A146T, E188D, I189V, D223G, S227T, or V235A.

The present disclosure provides CALB variants having an amino acid sequence as set forth in SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20 or SEQ ID NO: 22.

The present disclosure also provides nucleic acids encoding the CALB variants disclosed herein. In an aspect, the nucleic acid encoding a CALB variant is in a vector, such as an expression vector. The expression vector comprises regulatory elements including a secretion signal.

The present disclosure provides methods for expressing a CALB variant disclosed herein, wherein the method comprises transfecting an expression vector comprising the nucleic acid encoding a CALB variant into a host cell and culturing the host cell under conditions allowing expression of the CALB variant. The present disclosure also provides a method for preparing a CALB variant comprising expressing a CALB variant and obtaining the supernatant from the culture medium. The method can further comprise concentrating the supernatant comprising a CALB variant. The host cell for expressing the CALB variant can be a strain of *Bacillus subtilis*.

The present disclosure provides an expression vector for expressing CALB or CALB variant in a strain of *Bacillus*, wherein the expression vector comprises a nucleic acid encoding CALB or a CALB variant, one or more origins of replication for replication in *Bacillus*, a promoter, a secretion signal, and optionally a selectable marker. The promoter can be a constitutive promoter. In embodiments, the present disclosure provides an expression system comprising the expression vector, a host strain of *Bacillus*, and a culture medium.

The present disclosure provides culture medium comprising a non-carbohydrate micronutrient source, a buffering agent for maintaining pH of the medium at a range of about 5 to about 9, a non-hydrolyzable nonionic surfactant, and a nitrogen source. In embodiments, the culture medium comprises: about 0.1% to about 5% of a non-carbohydrate micronutrient source, relative to the total weight of the composition; a buffering agent for maintaining the pH at about 6 to about 8; about 0.01% to about 1% of a non-hydrolyzable nonionic surfactant, relative to the total weight of the composition; and about 0.1% to about 5% of a nitrogen source, relative to the total weight of the composition. In embodiments, the culture medium comprises: yeast extract, a buffering agent for maintaining the pH of the medium at 7, a block copolymer, and a nitrogen source comprising tryptone, hydrolyzed casein, casamino acids, peptone, soy peptone, nutrient broth, or meat extract.

The present disclosure provides a method of making CALB, WT or CALB variant, comprising transfecting the expression vector for expression in *Bacillus* into a *Bacillus*, and cultivating the *Bacillus* in a culture medium under conditions that allow expression and secretion of the polypeptide in the culture medium. In an aspect, the culture medium comprises a non-carbohydrate micronutrient source, a buffering agent for maintaining pH of the medium at a range of about 5 to about 9, a non-hydrolyzable nonionic surfactant, and a nitrogen source. In other aspects, the method comprises cultivating the *Bacillus* at a temperature of about 30° C. to about 42° C., about 35° C. to about 40° C., or about 37° C. In a further aspect, the method further comprises adding an additive for selection to the culture medium in the presence of a vector containing a selectable marker. The strain of *Bacillus* for expression of CALB, WT or CALB variant, can be *B. subtilis, B. cereus, B. brevis, B. licheniformis, B. stearothermophilus, B. pumilis, B. amyloliquefaciens, B. clusii,* or *B. megaterium*.

The method of making CALB or CALB variant disclosed herein can further comprise obtaining supernatant from the culture medium and concentrating the supernatant comprising CALB or CALB variant. The supernatant can be concentrated by ultrafiltration.

The present disclosure further comprises methods for identifying amino acid mutations in CALB that alter lipase activity, wherein the method comprises (a) obtaining crystal structure of a wild type (WT) CALB; (b) introducing one or more amino acid mutations into the WT CALB to obtain a CALB variant; (c) obtaining crystal structure of the CALB variant; (d) solvating the crystal structures of the WT CALB and the CALB variant into an implicit solvent; (e) performing molecular dynamic simulation on the structures to obtain resultant structures; (f) solvating the resultant structures into an explicit solvent; (g) performing molecular dynamic simulation on the resultant structures in the explicit solvent medium to obtain refined structures; (h) obtaining structural data for the refined structures of WT CALB and CALB variant; and (i) comparing the structural data obtained for the refined structures of the WT CALB and the CALB variant, to identify one or more amino acid mutations in CALB that alter lipase activity. In an aspect, the method disclosed herein comprises obtaining structural data for cavity volume of an active site of the WT CALB and the CALB variant. In other aspects, the method disclosed herein comprises obtaining structural data for solvent accessible surface area (SASA) of an active site of WT CALB and CALB variant. In a further aspect, the method comprises obtaining structural data for distance between center of mass of two residues of interest. The method disclosed herein further comprises correlating SASA, cavity volume, with the structure of CALB variant. The method further comprises correlating SASA of the CALB variant and its synthetic activity.

The method disclosed herein further comprises obtaining SASA of one or more amino acid positions of a catalytic triad of the WT CALB and obtaining SASA of one or more positions of a catalytic triad of the CALB variant, comparing the obtained SASA of an amino acid position of the catalytic triad of the WT CALB with the obtained SASA of a corresponding amino acid position of the catalytic triad of the CALB variant, and identifying a CALB variant that enhances lipase activity, such as its synthetic activity. The lipase activity can be a synthetic activity.

The present disclosure provides methods of catalyzing synthesis of a carboxylic acid ester, wherein one or more alcohols and one or more carboxylic acids or one or more carboxylic esters are reacted in the presence of a CALB variant disclosed herein to form a carboxylic acid ester. In embodiments, at least one or more carboxylic acids is a branched carboxylic acid, or at least one or more carboxylic acid esters are a branched carboxylic acid ester.

The present disclosure provides methods of catalyzing synthesis of an amide, wherein one or more carboxylic acids or carboxylic acid esters and one or more amines are reacted in the presence of a CALB variant disclosed herein to form an amide. In embodiments, at least one of the carboxylic acids is a branched carboxylic acid or at least one of the carboxylic acid esters is a branched carboxylic acid ester.

BRIEF DESCRIPTION OF THE DRAWINGS

FIG. 1 shows the vector map of pHT43. The vector includes: Pgrac promoter comprising groE promoter, lacO operator and gsiBSD sequence; ColE1 origin (ColE1 ori); ampicillin resistance ($Amp^R$), lac repressor (lacI gene); chloramphenicol resistance ($Cm^R$); and amyQ signal sequence (SamyQ).

DETAILED DESCRIPTION

Figure 2A:
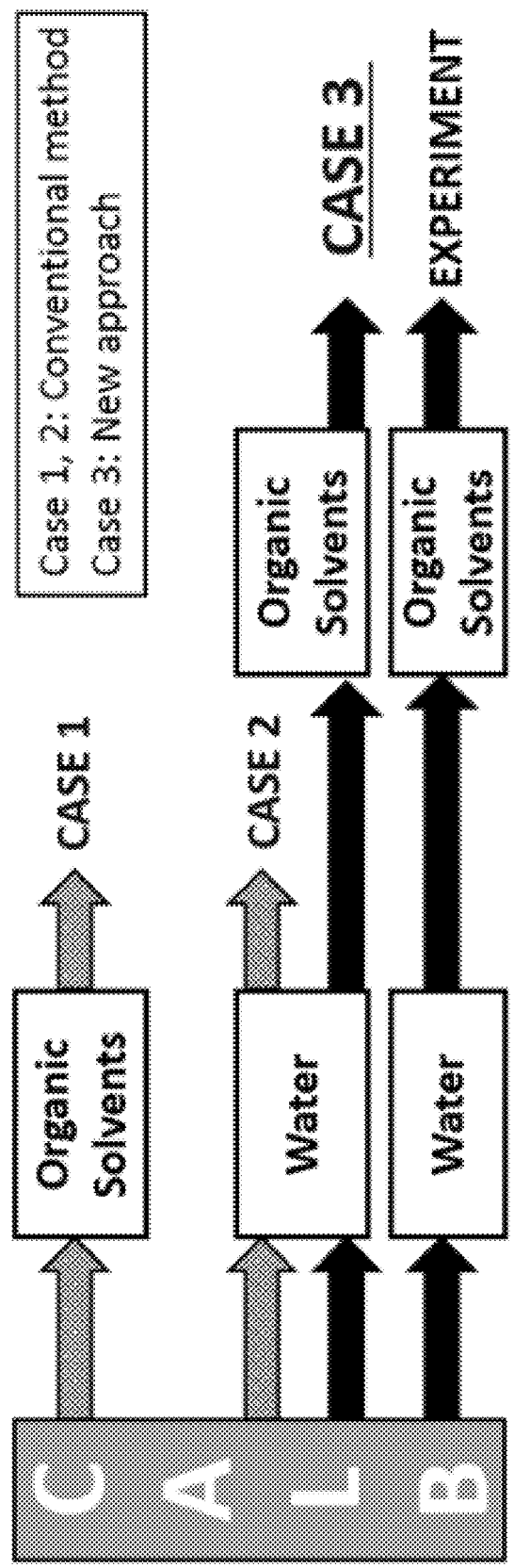
FIGS. 2A and 2B show: (A) The comparison between new approach (case 3) and two conventional computation approaches for MD simulations (case 1 and case 2). The three dimensional structure of CALB and (B) cavity volume and solvent accessible surface area of catalytic triad of variant 554 resulting from MD simulations using case 1, 2 and 3.

*Candida antarctica* lipase B (CALB) is an enzyme able to catalyze hydrolysis of esters, and more significantly, synthesis reactions, such as direct esterification, transesterification, and amidation of a wide range of alcohols and acids. The native CALB synthesis activity needs improvement for use at a large scale or for non-specialty products, especially for hindered substrates. The terms "wild type" and "native" when referring to CALB are used interchangeably throughout the present disclosure.

The present disclosure is based in part on the identification of specific amino acid changes in the wild type (WT) or parent protein sequence of CALB that lead to an increase in the synthesis activity of the enzyme of greater than about two fold, about 2 to 15 fold, or about 3 to 12 fold over the WT CALB. Additionally, the present disclosure is based on the development of methods that allow for the generation and characterization of these enzyme variants using novel computational methods and effective enzyme expression in a prokaryotic host, such as Bacillus.

The crystal structure of CALB has been solved experimentally and deposited in the RCSB Protein Data Bank (PDB) as structure 1TCA. 1TCA represents the structure of the native amino acid sequence of CALB in an aqueous environment, which would occur during synthesis and secretion of the enzyme by a microbial host, and also when the enzyme is catalyzing a hydrolytic reaction. However, when the enzyme is isolated, dried, and used to catalyze a condensation reaction, such as esterification or amidation, then an implicit "aqueous" solvent model is not applicable.

The active site of CALB is a triad consisting of residues S105, D187 and H224. The terms "active site" and "catalytic site" are used interchangeably throughout the present disclosure. The present disclosure is based in part on the discovery that the structural changes that accompany specific amino acid sequence changes, especially near the active site residues, result in a significant change to the protein structure when modelled in explicit solvent, mimicking the organic esterification reaction mixture. Provided herein are various CALB variants comprising amino acid alterations. As an example, the structure of the novel CALB variants 529 (D223G, S227T) and 554 (E188D, D223G, S227T) predict a more open substrate cavity than the WT CALB or the CALB variant with D223G, with better access to the active site in non-aqueous conditions, such as during synthesis reactions.

As used herein, the term CALB includes both WT CALB and CALB variants.

Protein engineering requires expression of a catalytically active protein in a microbial system. However, CALB is not expressed effectively in prokaryotic expression systems as a secreted protein. To address the limitation of eukaryotic and E. coli expression hosts, the present disclosure provides an improved expression system for CALB using Bacillus subtilis (Bsub) as the host. This expression system is suitable for high-throughput screening of enzyme variants. While there are no published reports of CALB expression in Bsub, the components of a suitable expression system can be assembled or built from components available from commercial suppliers, published reports and database sequences, or requested from academic institutions and culture collections. Provided herein is a novel bacterial expression system for expressing large quantities of active CALB.

Expression system components include a host strain of Bacillus, an expression vector, expression media and growth conditions. The ideal expression system results in constitutive, high level expression of catalytically active protein secreted into the media without a deleterious impact on the host or the need to shuttle DNA between multiple hosts. The host should have a high transformation efficiency using the expression vector.

Any suitable Bacillus host may direct the expression of CALB, the WT or the variant form. In embodiments, enzyme expression in the host strain Bsub WB800N (MoBiTec) benefits from the deletion of eight extracellular proteases from the genome. In other embodiments, the CALB was expressed in strain BGSC 1S141. The expression vector can include a nucleic acid encoding CALB, a Bacillus origin of replication, a promoter, a secretion signal, and optionally a selection marker. As an example, the expression vector pHT43 allows inducible expression of the target protein as a translational fusion with an extracellular amylase, which is secreted via the sec system in Bacillus. Constitutive expression is preferred, as it eliminates the need to induce expression, and avoids any variation in expression caused by induction timing or conditions. Various methods for B. subtilis transformation are available, including the protocol supplied with the host strain, protocols based on electroporation and protoplast transformation, and protocols based on natural competence of B. subtilis. The latter method takes advantage of the natural competence of B. subtilis to incorporate DNA, and both closed circular and linear DNA can be successfully introduced. Long linear repeats of vector and insert can be made and assembled via PCR, and introduced directly into Bsub competent cells. In this case, the shuttle vector features (coliform origin of replication and antibiotic resistance marker for E. coli host) would be non-essential vector components.

Factors that impact CALB expression in the Bacillus system include media and conditions such as growth temperature, nitrogen source and content, the presence of a non-hydrolyzable surfactant, and the biomass density of the inoculum. Surprisingly, the presence of a carbohydrate carbon source or dense inoculum reduces lipase expression/activity in B subtilis. The secreted lipase is readily isolated from the culture supernatant and used to catalyze synthesis reactions. Provided herein are novel culture media comprising a non-carbohydrate micronutrient source, a buffering agent for maintaining pH of the media at a range of about 5 to about 9, a non-hydrolyzable nonionic surfactant, and a nitrogen source The disclosure is also based on the discovery of a new strategy to elucidate the key mutation sites via molecular dynamic (MD) simulations. This strategy provides a two-step approach: (1), MD simulation of a protein and/or its mutants are performed in implicit aqueous solvent condition and, followed by (2) a simulation using explicit solvents which are equivalent to the solvents used in experiment. Crystal structure of CALB that was used in the simulations was obtained from Protein Data Bank (PDB, Code: 1TCA) and mutations of residues in CALB were introduced using Discovery Studio 4.0 software (Accelrys Software Inc.). This approach permitted the discovery of front (I189 and I285) and side (E188 and L278) gates that directly control the access to the catalytic triad. It was also discovered that the distance between these gating residues can be controlled through specific mutations described herein. The mutations change the size of the catalytic cavity and accessibility of the catalytic triad and consequently control the activity. The analysis of the simulations that assisted this discovery include solvent accessible surface area of the catalytic amino acids, cavity volume, the distance between gating residues and stability of the CALB structure.

Provided herein are new computational protocols that enable accurate exploration of the effect of mutations and solvent environment on the structure of CALB that can be used for prediction of new mutation sites and obtaining novel variants with improved enzyme activity.

The present disclosure provides CALB variants having an amino acid sequence that is different from the WT CALB. The terms "CALB variant," "modified CALB," and "CALB mutant" are used interchangeably throughout the disclosure to refer to a CALB with an amino acid sequence that is different from the WT CALB. The CALB variant can have altered physical and functional activity as compared to a WT CALB. Physical activity can include stability, such as thermostability. Functional activity can include lipase activity, such as hydrolytic activity and synthetic activity, for example, catalyzing the amidation, direct esterification, and transesterification. The CALB variants can have improved activity for catalyzing synthesis reactions as compared to a WT CALB. The CALB variants can have any increase in activity for catalyzing synthesis reactions. The CALB variants can have approximately a 2 fold, 3 fold, 4 fold, 5 fold, 6 fold, 7 fold, 8 fold, 9 fold, 10 fold, 15 fold, or 20 fold increase in activity for catalyzing reactions, such as synthesis reactions. The CALB variants provided herein catalyzes synthesis reactions, such as amidation, direct esterification, and transesterification. The lipase activity of CALB variants can be measured by any synthesis assay that can determine the reactants or products of a condensation reaction is suitable. The esterification reaction to generate esters or amides such as octyl benzoate, octyl octanoate or octyl octanamide, where the depletion of reactants and appearance of products can be detected by liquid or gas chromatography. The depletion of reactants can also be monitored by titration or hydroxyl number. The synthesis activity can be measured as PLU or propyl laurate units (Chow et al., PLoS One 2012, 7(10), e47665). There is no external reference for the benzoate ester assay. The synthesis activity of CALB can be measured by the benzoic acid (BZA) esterification assay.

The term "CALB variant" as used herein refers to a CALB that has been modified to comprise an alteration, such as a substitution, insertion, and/or deletion, of one or more amino acid residues at one or more specific positions of the polypeptide of SEQ ID No: 2 (WT CALB). The nucleic acid or polynucleotide encoding the CALB variant can be obtained through human intervention by modification of the polypeptide coding sequence disclosed in SEQ ID No: 1 (WT CALB nucleic acid). The amino acid substitution, insertion, and/or deletion can be conservative or non-conservative. The CALB variant has an activity that is different from the WT CALB. The activity can be for catalyzing synthesis reactions.

It was a surprising discovery that amino acid alterations near the active triad site, S105, D187, and H224 result in CALB variants having altered activity or stability. The variants provided herein can have one or more, two or more, three or more, four or more, five or more, six or more, seven or more, eight or more, nine or more, or ten or more amino acid alterations. Provided herein are CALB variants having one or more amino acid alterations at position 141, 146, 188, 189, 223, 227, or 235 of SEQ ID NO: 2. In an aspect, the one or more amino acid substitutions is: a substitution at A141 to a threonine (T); a substitution at A146 to a threonine (T); a substitution at E188 to an aspartic acid (D); a substitution at I189 to a valine (V); a substitution at D223 to a glycine (G); a substitution at S227 to a threonine (T); and a substitution at V235 to an alanine (A). In other aspect, the CALB variants provided herein have two to seven amino substitutions, wherein the substitutions are at position 141, 146, 188, 189, 223, 227, or 235 of SEQ ID NO: 2.

The present disclosure provides CALB variants as shown in Table 1.

TABLE 1

CALB Variants

| Variant | A141 | A146 | E188 | I189 | D223 | S227 | V235 | SEQ ID NO: |
|---|---|---|---|---|---|---|---|---|
| 529 |  |  |  |  | G | T |  | 4 |
| 554 |  |  | D |  | G | T |  | 6 |
| 857 | T |  | D |  | G | T |  | 8 |
| 984 | T | T | D |  | G | T |  | 10 |
| 940 | T |  | D | V | G | T |  | 12 |

TABLE 1-continued

CALB Variants

| Variant | A141 | A146 | E188 | I189 | D223 | S227 | V235 | SEQ ID NO: |
|---|---|---|---|---|---|---|---|---|
| 880 | T |  | D |  | G | T | A | 14 |
| 959 | T | T | D |  | G | T | A | 16 |
| 965 | T | T | D | V | G | T |  | 18 |
| 953 | T |  | D | V | G | T | A | 20 |
| 963 | T | T | D | V | G | T | A | 22 |

In embodiments, the present disclosure provides fusion proteins comprising a CALB variant disclosed herein and a heterologous peptide or polypeptide. The heterologous sequences can, for example, include sequences designed to facilitate purification, e.g. histidine tags, and/or visualization of recombinantly-expressed proteins. Other non-limiting examples of fusion proteins include those that permit display of the CALB variant on the surface of a phage or a cell, fusions to intrinsically fluorescent proteins, such as green fluorescent protein (GFP), fusion to signal peptides to direct polypeptide processing and export, fusion to cellulose binding module(s), fusion to dockerin domain(s), fusion to cohesion domain(s), fusion to fibronectin-like domain(s), fusions to the IgG Fc region, and the like. The fusions can be direct or can be by way of intervening peptide linker regions/domains.

The present disclosure provides peptides and polypeptides that are fragments of CALB variants of the CALB variants disclosed herein. The peptides and polypeptides of the CALB variants disclosed herein are functionally active and have synthesis activity. In embodiments, these peptides include at least 25, 30, 35, 40, 45, 50, 60, 70, 80, 90, 100, 150, 200, 250, 300, or more contiguous amino acids of a CALB variant disclosed herein. As an example, the first 34 amino acids can be removed from a CALB variant disclosed herein. The peptides and polypeptides include at least the catalytic domain of a CALB variant and/or possess functional activity, such as synthesis activity. In certain embodiments, the peptides and polypeptides comprising the catalytic domain of the variant cellulolytic enzyme are provided and possess functional activity, such as synthesis activity. The functional activity of the peptides can be the same as the full length CALB variant.

Also disclosed herein are nucleic acids encoding CALB variants having a 2 fold, 3 fold, 4 fold, 5 fold, 6 fold, 7 fold, 8 fold, 9 fold, 10 fold, 15 fold, or 20 fold increase in activity for catalyzing synthesis reactions, such as esterification, amidation, and transesterification. The nucleic acid or polynucleotide can be a DNA or RNA. The DNA can be a cDNA.

In embodiments, the nucleic acids provided herein encode a CALB variant having an amino acid sequence as set forth in SEQ ID NO: 4, 6, 8, 10, 12, 14, 16, 18, 20, or 22. In other embodiments, the nucleic acids provided herein encoding a CALB variant has a nucleic acid sequence as set forth in SEQ ID NO: 3, 5, 7, 9, 11, 13, 15, 17, 19, or 21.

The CALB variants provided herein have at least about 80%, 85%, 90%, 95%, 96%, 97%, 98%, or 99% sequence identity with the amino acid sequence of the WT CALB, wherein the CALB variants have a 2 fold, 3 fold, 4 fold, 5 fold, 6 fold, 7 fold, 8 fold, 9 fold, 10 fold, 15 fold, or 20 fold increase in activity for catalyzing reactions, such as synthesis reactions. The CALB variants provided herein catalyzes synthesis reactions, such as esterification, amidation, and transesterification.

The relatedness between two amino acid sequences or between two nucleotide sequences is described by the parameter "identity". For purposes of the present disclosure, the degree of identity between two amino acid sequences is determined using the Needleman-Wunsch algorithm as implemented in the Needle program of the EMBOSS package (EMBOSS: The European Molecular Biology Open Software Suite), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the—nobrief option) is used as the percent identity and is calculated as follows:

(Identical Residues×100)/(Length of Alignment–
Total Number of Gaps in Alignment)

In embodiments, the nucleic acids encoding CALB variants provided herein have at least 80%, 85%, 90%, 95%, 96%, 97%, 98%, or 99% sequence identity with the nucleic acid encoding the WT CALB (SEQ ID NO: 1). Moreover, the nucleic acids encoding the CALB variants hybridize at least under low stringency conditions to SEQ ID NO: 1.

For purposes of the present disclosure, the degree of identity between two deoxyribonucleotide sequences is determined using the Needleman-Wunsch algorithm as implemented in the Needle program of the EMBOSS package, preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the—nobrief option) is used as the percent identity and is calculated as follows:

(Identical Deoxyribonucleotides×100)/(Length of
Alignment–Total Number of Gaps in Alignment)

As disclosed herein, the CALB variants disclosed herein have an amino acid sequence comprising two or more amino acid substitutions at a position in a sequence corresponding to any of positions 141, 146, 188, 189, 223, 227 or 235 of SEQ ID NO: 2, wherein (a) the variant has about 2 fold to 20 fold increase in activity for catalyzing synthesis reactions such as esterification, amidation, and transesterification; (b) the variant has an amino acid sequence having at least 80% sequence identity with SEQ ID NO: 2 (WT CALB); (c) the nucleic acid encoding the CALB variant hybridizes under at least low stringency conditions with the nucleic acid encoding WT CALB (SEQ ID NO: 1) or its complementary strand; and (d) the variant is encoded by a nucleic acid comprising a sequence having at least 80% identity with SEQ ID NO: 1.

In an aspect, the CALB variant is encoded by a nucleic acid sequence that hybridizes under very low stringency conditions, low stringency conditions, medium stringency conditions, medium-high stringency conditions, high stringency conditions, or very high stringency conditions with SEQ ID NO: 1 or its complementary strand. The stringency conditions are provided in Sambrook et al. (J. Sambrook, E. F. Fritsch, and T. Maniatis, 1989, Molecular Cloning, A Laboratory Manual, 2d edition, Cold Spring Harbor, N.Y.), which is incorporated by reference in its entirety.

In an aspect, the preparation of a variant CALB can be achieved by preparing a nucleic acid sequence by modifying the nucleic acid sequence encoding the WT CALB, transforming the nucleic acid sequence into a suitable host, and expressing the modified sequence to form the variant CALB. In other aspects, the variant CALB can be prepared by expressing the nucleic acid sequence encoding the WT CALB in an in vitro expression system without the need for a host. In embodiments the variant CALB can be chemically synthesized.

CALB variants can be prepared according to any mutagenesis procedure known in the art, such as site-directed mutagenesis, synthetic gene construction, semi-synthetic gene construction, random mutagenesis, shuffling, etc.

Site-directed mutagenesis is a technique in which one or several mutations are created at a defined site in a nucleic acid molecule encoding the WT CALB polypeptide. The technique can be performed in vitro or in vivo.

Site-directed mutagenesis can be accomplished in vitro by PCR involving the use of oligonucleotide primers containing the desired mutation. Site-directed mutagenesis can also be performed in vitro by cassette mutagenesis involving the cleavage by a restriction enzyme at a site in the plasmid comprising a nucleic acid encoding the WT CALB polypeptide and subsequent ligation of an oligonucleotide containing the mutation in the polynucleotide. Usually the restriction enzyme that digests at the plasmid and the oligonucleotide is the same, permitting sticky ends of the plasmid and insert to ligate to one another. See, for example, Scherer & Davis (1979 PNAS USA 76:4951-4955); and Barton et al. (1990 Nucleic Acids Research 18:7349-4966).

Site-directed mutagenesis can be accomplished in vivo by methods known in the art. See, for example, U.S. Patent Application Publication 2004/0171154; Storici et al. (2001 Nature Biotechnology 19:773-776); Kren et al. (1998 Nat. Med. 4:285-290); and Calissano & Macino (1996 Fungal Genet. Newslett. 43:15-16). Any site-directed mutagenesis procedure can be used for preparing the CALB variants. There are many commercial kits available that can be used to prepare variants of a WT CALB.

Single or multiple amino acid substitutions, deletions, and/or insertions can be made and tested using known methods of mutagenesis, recombination, and/or shuffling, followed by a relevant screening procedure, such as those disclosed by Reidhaar-Olson & Sauer (1988 Science 241: 53-57); Bowie & Sauer (1989 PNAS USA 86:2152-2156); WO95/17413; or WO95/22625. Other methods that can be used include error-prone PCR, phage display (Lowman et al. 1991 Biochem. 30:10832-10837; U.S. Pat. No. 5,223,409; WO92/06204) and region-directed mutagenesis (Derbyshire et al., 1986, Gene 46:145; Ner et al., 1988, DNA 7:127).

In various embodiments, nucleic acids encoding one or more of the CALB variants described herein are inserted into vectors suitable for expressing the CALB variants in a host cell. In such vectors, the nucleic acid sequence encoding the CALB variant is operably linked to one or more promoters and/or other regulatory sequences.

The term "operably linked" refers herein to a configuration in which a control sequence is appropriately placed at a position relative to the nucleic acid encoding the variant CALB sequence such that the control sequence influences the expression of a variant CALB polypeptide.

As used herein, the term "expression" includes any step involved in the production of the polypeptide including, but not limited to, transcription, post-transcriptional modification, translation, post-translational modification, and secretion.

An "expression vector" refers to a nucleic acid construct comprising a nucleic acid sequence (e.g., DNA sequence) that is operably linked to a suitable control sequence capable of effecting the expression of the nucleic acid in a suitable host. Such control sequences may include a promoter to effect transcription, an optional operator sequence to control transcription, a sequence encoding suitable ribosome-binding sites on the mRNA, and sequences that control termination of transcription and translation. Different cell types are typically used with different expression vectors. For example, an illustrative promoter for vectors used in *Bacillus* spp. is the groE, AprE, or Pgrac promoter; an illustrative promoter used in *E. coli* is the Lac promoter, an illustrative promoter used in *Saccharomyces* spp. is PGK1, an illustrative promoter used in *Aspergillus* spp. glaA, and an illustrative promoter for *Trichoderma* spp. is cbhI. In embodiments the vector may be a plasmid, a phage particle, or simply a potential genomic insert. Once transformed into a suitable host, the vector may replicate and function independently of the host genome, or may, under suitable conditions, integrate into the genome itself. Expression techniques are known in the art and are described generally in, for example, Sambrook.

Nucleic acids encoding the CALB variants described herein can be incorporated into any of a variety of expression vectors suitable for expressing a polypeptide. Any vector that expresses genetic material into a cell can be used.

When incorporated into an expression vector, the nucleic acid sequence encoding the desired CALB variant is operatively linked to an appropriate transcription control sequence (promoter) to direct mRNA synthesis, e.g., T5 promoter. Examples of such transcription control sequences include the cauliflower mosaic virus (CaMV) and figwort mosaic virus (FMV), SV40 promoter, *E. coli* lac or trp promoter, phage lambda $P_L$ promoter, tac promoter, T7 promoter, and the like. In bacterial host cells, suitable promoters include the promoters obtained from the *E. coli* lac operon, *Streptomyces coelicolor* agarase gene (dagA), a gene from a *Bacillus* sp., such as, for example, the *Bacillus subtilis* levansucranse gene (sacB) or gro E gene, the *Bacillus licheniformis* alpha-amylase gene (amyl), the *Bacillus megaterium* InhA gene, the *Bacillus stearothermophilus* maltogenic amylase gene (amyM), the *Bacillus amyloliquefaciens* alpha-amylase gene (amyQ), *Bacillus subtilis* xylA and xylB genes, the xylose promoter (Pxyl) from *Bacillus megaterium*, the promoter obtained from the prokaryotic beta-lactamase gene, and so forth.

In various embodiments, an expression vector optionally contains a ribosome binding site for translation initiation, and a transcription terminator, such as PinII. The vector also optionally includes appropriate sequences for amplifying expression, such as an enhancer. The vector also includes regions for vector replication, as examples, ORF-1, ORF-2, and ORF-3 for replication in *bacillus*.

In various embodiments the vector or DNA construct may also generally include a signal peptide coding region that codes for an amino acid sequence linked to the amino terminus of a polypeptide and which directs the encoded polypeptide into the cell's secretory pathway. Suitable signal peptides include, but are not limited to the *Bacillus megaterium* penicillin G acylase signal peptide sequence.

Other illustrative signal peptide coding regions for bacterial host cells may be obtained from the genes of *Bacillus* NCIB 11837 maltogenic amylase, *B. stearothermophilus* alpha-amylase, *B. licheniformis* subtilisin, B. beta-lactamase, *B. stearothermophilus* neutral proteases (nprT, nprS, nprM) and *B. subtilis* prsS. Further illustrative signal sequences are described in Simonen and Palva (1993, Microbiological Reviews 57: 109-137). Effective signal peptide coding regions for filamentous fungal host cells include but are not limited to the signal peptide coding regions obtained from *Aspergillus oryzae* TAKA amylase, *Aspergillus niger* neutral amylase, *Aspergillus niger* glucoamylase, *Rhizomucor miehei* asparatic proteinase, *Humicola insolens* cellulase and *Humicola lanuginosa* lipase. Variants of these signal peptides and other signal peptides are suitable, as well as expression mutants thereof having one or more silent mutations.

In various embodiments the expression vectors optionally contain one or more selectable marker genes to provide a phenotypic trait for selection of transformed host cells. Suitable marker genes include those coding for antibiotic resistance such as, ampicillin, kanamycin, chloramphenicol, or tetracycline resistance. Further examples include the antibiotic spectinomycin or streptomycin (e.g., the aada gene), the streptomycin phosphotransferase (SPT) gene coding for streptomycin resistance, the neomycin phosphotransferase (NPTII) gene encoding kanamycin or geneticin resistance, the hygromycin phosphotransferase (HPT) gene coding for hygromycin resistance. Additional selectable marker genes include dihydrofolate reductase or neomycin resistance for eukaryotic cell culture, and tetracycline or ampicillin resistance in *E. coli*.

The vector may further contain genetic elements that facilitate integration by either homologous or non-homologous recombination. Genetic elements that facilitate integration by homologous recombination have sequence homology to targeted integration sites in the genomic sequence of the desired expression host cell. Genetic elements or techniques which facilitate integration by non-homologous recombination include restriction enzyme-mediated integration (REMI), transposon-mediated integration, and other elements and methods that are well known in the art.

In embodiments, the nucleic acid sequence encoding the CALB variants described herein can also be fused, for example, in-frame to nucleic acids encoding a secretion/localization sequence, to target polypeptide expression to a desired cellular compartment, membrane, or organelle of a cell, or to direct polypeptide secretion to the periplasmic space, to the cell membrane or cell wall, or into the cell culture media. Such sequences are known to those of skill, and include secretion leader peptides, organelle targeting sequences (e.g., nuclear localization sequences, endoplasmic reticulum (ER) retention signals, mitochondrial transit sequences, peroxisomal transit sequences, and chloroplast transit sequences), membrane localization/anchor sequences (e.g., stop transfer sequences, GPI anchor sequences), and the like.

The expression vector includes elements for inducible or constitutive expression of the CALB variant.

"Host strain" or "host cell" means a suitable host for expressing nucleic acids comprising an expression vector as described herein. Illustrative host cells include prokaryotic or eukaryotic hosts, including any transformable microorganism in which expression can be achieved. The host cell may be chosen from eukaryotic or prokaryotic systems, such as for example bacterial cells, (Gram negative or Gram positive), yeast cells (for example, *Saccharomyces cereviseae* or *Pichia pastoris*), animal cells (such as Chinese hamster ovary (CHO) cells), plant cells, and/or insect cells using baculovirus vectors. In some embodiments, the host cells for expression of the polypeptides include, and are not limited to, those taught in U.S. Pat. Nos. 6,319,691, 6,277, 375, 5,643,570, or 5,565,335, each of which is incorporated by reference in its entirety, including all references cited within each respective patent.

Examples of host strains include, but are not limited to, Bacillus, Escherichia coli, Trichoderma reesei, Saccharomyces cereviseae, Aspergillus niger, and the like. Specific examples of *Bacillus* include *B. subtilis, B. cereus, B. brevis, B. licheniformis, B. stearothermophilus, B. pumilis, B. amyloliquefaciens, B. clusii,* or *B. megaterium.*

Recombinant expression vectors can be introduced into host cells to produce a transformed host cell. These cells are useful experimental systems. Accordingly, the present disclosure provides a host cell comprising a recombinant expression vector for expression of the CALB variants disclosed herein. The term "transformed host cell" is intended to include prokaryotic and eukaryotic cells which have been transformed or transfected with a recombinant expression vector of the invention. Prokaryotic cells can be transformed with nucleic acid by, for example, electroporation or calcium-chloride mediated transformation. Nucleic acid can be introduced into mammalian cells via conventional techniques such as calcium phosphate or calcium chloride co-precipitation, DEAE-dextran-mediated transfection, lipofectin, electroporation or microinjection. Suitable methods for transforming and transfecting host cells can be found in Sambrook et al., and other such laboratory textbooks. Suitable host cells include a wide variety of prokaryotic and eukaryotic host cells. For example, the peptides of the invention may be expressed in bacterial cells such as *E. coli, Pseudomonas, Bacillus subtillus,* insect cells (using baculovirus), yeast cells or mammalian cells. Other known suitable host cells can also be used.

The nucleic acids encoding the CALB variant can be codon optimized for the host used to express the CALB variant.

The present disclosure also provides a novel expression system for expressing WT CALB and CALB variant. The expression system is based on a bacterial expression system using a *Bacillus* host, for expressing large quantities of active CALB polypeptide. Examples of *Bacillus* host include but are not limited to *B. subtilis, B. cereus, B. brevis, B. licheniformis, B. stearothermophilus, B. pumilis, B. amyloliquefaciens, B. clusii,* and *B. megaterium.*

The bacterial expression system disclosed herein provides the following benefits over other known expression systems for eukaryotic lipases like CALB:

There is no need to codon-optimize the protein coding region for the host.

There is no need to shuttle expression constructs through an intermediate host like *E. coli.*

The lipase is effectively expressed and secreted directly into the media, both liquid and solid, so there is no need to include a cell lysis step.

The lipase can be constitutively expressed, eliminating the need for induction.

The lipase is correctly folded into a form able to catalyze hydrolysis and synthesis reactions, including transesterification, direct esterification and amidation reactions.

Maximum expression levels can be achieved in as little as 18 hours of liquid culture.

The new bacterial system is able to express the lipase under a variety of conditions, and in a relatively simple and inexpensive media. Factors that impact lipase expression in the system include growth temperature, nitrogen source and content, the presence of a non-hydrolyzable surfactant, and the biomass density of the inoculum. Surprisingly, the presence of a carbohydrate carbon source or dense inoculum reduces lipase expression/activity.

For expressing secreted recombinant CALB in a prokaryotic host of the genus *Bacillus*, it was discovered that the expression media should contain a source of micronutrients and vitamins, a complex nitrogen source, a non-hydrolyzable nonionic surfactant, and optionally an additive for selection, if a selectable marker is present on the expression vector. It was also discovered that a carbohydrate source, such as glucose, sucrose, glycerol, and the like, should not be present in the expression media.

The expression media base disclosed herein comprises a source of micronutrients and vitamins, such as yeast extract. The concentration of yeast extract can vary from about 0.1% to about 5%, about 0.2% to about 4%, about 0.3% to about 3%, about 0.4% to about 2% or about 0.5% to about 1%. Synthetic defined media may also be sufficient as a base, such as that described in Demain (Minimal media for quantitative studies with *Bacillus subtilis*, 1956, Journal of Bacteriology, vol 75 p. 517).

The expression media disclosed herein comprises a complex nitrogen source. Complex nitrogen sources include yeast extract, tryptone, hydrolyzed casein, casamino acids, peptone, soy peptone, nutrient broth, and meat extract. A defined mixture of amino acids can also be used. The concentration of nitrogen source can vary from about 0.1% to 5%, about 0.2% to about 4%, about 0.3% to about 3%, or about 0.5% to about 2%.

The expression media disclosed herein comprises a non-hydrolyzable nonionic surfactant. Typical surfactants used in biological systems, such as Span and Tween, contain ester bonds that can be hydrolyzed by the expressed lipase, rendering them non-functional as a surfactant. Instead, the surfactant additive must not be hydrolysable, but must also not denature the expressed enzyme. Such surfactants include the block-copolymer surfactants, also known as poloxamers (Pluronics™). Examples of poloxamer-type block copolymer include but are not limited to Pluronic L31™, L35™, and F68™. The poloxamer surfactants differ in monomer composition and molecular weight. The poloxamers tested improved recovered activity of secreted lipase. The concentration of the non-hydrolyzable surfactant in the media is about 0.01% to about 1%, about 0.02% to about 0.8%, about 0.03% to about 0.6%, about 0.04% to about 0.4%, or from 0.05 to about 0.2%.

An additive for selection may be included in the media, if a selectable marker is present on the expression vector.

A fermentable carbohydrate source (glucose, sucrose, glycerol, etc) should be absent from the expression media.

Provided herein is an expression media comprising a source of micronutrients and vitamins, a complex nitrogen source, a non-hydrolyzable nonionic surfactant, and optionally an additive for selection.

It was also discovered that the optimal expression conditions include buffering the expression media to a neutral pH and maintaining the expression system at a temperature of about 30° C. to about 42° C.

In an aspect, the expression system comprises an expression media buffered at between about pH 5 and about pH 9, between about pH 6 and about pH 8, or at about pH 7.

In other aspects, the expression system is maintained at a temperature of between about 30° C. to about 42° C., about 35° C. to about 40° C., or about 37° C. for expression of CALB.

The present disclosure provides a method for expressing a CALB comprising the use of a novel expression system for optimal expression of CALB. The expression system comprises an expression vector for expressing a CALB in *Bacillus*. The CALB is expressed under optimal conditions such as in a novel culture medium buffered to a neutral pH and at a temperature of between about 30° C. to about 42° C.

Provided herein are expression vectors for expressing a CALB in *Bacillus* comprising a nucleic acid encoding a CALB, one or more origins of replication for replication in *Bacillus*, a promoter, a secretion signal, and optionally a selectable marker.

Provided herein are culture media comprising about 0.1% to about 5% of a non-carbohydrate micronutrient source and vitamins, a buffering agent for maintaining the pH at about 6 to about 8, about 0.01% to about 1% of a non-hydrolyzable nonionic surfactant, and about 0.1% to about 5% of a nitrogen source, All amounts of the components of the culture media are relative to the total weight of the composition.

In embodiments, the methods for expressing CALB provided herein further comprise concentrating the expressed CALB. In an aspect, the expressed CALB can be concentrated by precipitation or chromatography. In other aspects, the expressed CALB is concentrated by ultrafiltration through a filter with a molecular weight cut-off smaller than the size of the enzyme.

The present disclosure provides compositions comprising CALB variants and a carrier. The composition can be a pharmaceutical composition, in which case the carrier is a pharmaceutically acceptable carrier.

The embodiments of any of the products (CALB variants), compositions, or methods disclosed herein can consist of or consist essentially of—rather than comprise/include/contain/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb. As used herein, the term "consisting essentially of" indicates that the product or composition necessarily includes the listed ingredients and is open to unlisted ingredients that do not materially affect the basic and novel properties of the invention. As an example, peptides of CALB variants can consist of or consist essentially of a number of contiguous amino acids of a full length amino acid sequence.

The present disclosure provides methods for analyzing molecular interactions in solution for accurate determination of the effect of mutations and solvent environment on the structure of CALB. The information obtained from the analysis can be used to predict new mutation sites for improving enzyme activity.

In embodiments, the present invention provides computational tools and structure-function analysis such as molecular dynamics (MD) simulations for obtaining structural data including cavity volume of a group of amino acids and solvent accessibility of functional groups (SASA) in a protein, such as CALB and its variants. MD numerically solve Newton's equations of motion of atoms in the molecular system to obtain information on its time-dependent properties, which gives an insight into conformational changes of bio-materials, such as proteins and DNA. For protein engineering, MD simulations have been widely used as tools for evaluating the structural properties of residues in proteins and for the selection of key mutation sites for better enzyme activity and stability.

In an aspect, the approach employed involves combining structural information of the CALB polypeptide derived from X-ray crystallography with computational modeling and simulation of the wild type and variant forms of the catalytic triad domain. This approach enabled obtaining structural and functional data of the potential role of individual amino acids and their cooperative action in the catalytic triad domain. The structural and functional data obtained from multiple variants along with the empirical data of stability and other chemical and physical properties of CALB and its variants permitted a determination of the correlation of structure and function and the identification of specific amino acid responsible for structural changes around the catalytic pocket of CALB.

Previous computational studies have mainly used water as a solvent to explain the effect of mutations in organic solvents or to suggest mutation sites for the experiment which has to be performed in non-aqueous systems, such as trans-esterification reactions. Same approach has been used for MD simulations on *Candida Antarctica* Lipase B (CALB) and its mutants: simulations have been always performed in aqueous solutions regardless of the solvents used in experiment. Even though water is a major contributor to a protein's 3-D structure and therefore this conventional approach has helped in the guidance of mutation studies, it is expected that using water as a solvent for MD simulations cannot represent the rational structures of proteins or their mutants in non-aqueous solutions, thus leading to inaccurate selections of important mutation sites.

The present disclosure provides a novel approach to MD simulation of CALB and its variants. The method provided herein involves a two step approach to accurately determine important mutation sites for improved CALB activity. MD simulation of CALB and its variants are first performed in an implicit aqueous solvent condition. Subsequently, a MD simulation is performed using explicit solvents, which are equivalent to the solvents used in synthesis reactions that CALB catalyzes, such as esterification, amidation, and transesterification.

The present method employs MD to simulate the CALB structure, to evaluate the intrinsic dynamic nature of the structure, especially the active site, in an aqueous environment and in the organic (explicit) solvents. Molecular dynamics simulations track the dynamic trajectory of a molecule resulting from motions arising out of interactions and transient forces acting between all the atomic entities in the protein and its local environment, in this case the atoms constituting the CALB or its variants and their surrounding water (implicit environment) and/or organic (explicit environment) molecules. This analysis provides an understanding of the differences of each CALB variant as compared to the WT CALB, with respect to properties, such as solvent accessible surface area (SASA) of the catalytic amino acids, cavity volume, distance between gating residues, and stability of the CALB structure, thus allowing identification of amino acids for mutation to improve functional activity, for example, synthesis reaction of CALB.

The method disclosed herein is based on extensive expertise in modeling CALB and its variants and the use of molecular dynamics (MD) simulations to evaluate the influence of solvents on WT CALB activity. The studies performed identified specific amino acids responsible for structural changes around the catalytic pocket of CALB and correlated these changes with the experimental observations. As an example, it was shown that access to the catalytic site and the volume of the cavity is correlated with the activity of the enzyme.

CALB is an enzyme catalyst used for the production of esters. Using the method disclosed herein, variants having lipase activity, such as synthesis activity, were produced. These variants were shown, as an example, to esterify benzoic and/or 2-ethylhexanoic acid. The methods disclosed herein provides identification of more variants with improved activity or substrate preference more easily.

Accordingly, understanding the structure/function relationship of CALB variants is important to predicting their utility in making esters. Experimental data collected for the active variants based on model esterification reactions, and the sequence variations can be mapped onto the native protein structure. The method disclosed herein provides an understanding of the basis of the activity changes, and ultimately to more accurately predict other variants for study.

The method provided herein is an improved method for performing molecular dynamics (MD) simulations of WT CALB and its variants. The method provides more accurate information on structure/function relationship CALB which enables discovery of CALB variants with improved synthesis activity.

The data obtained from MD simulations are analyzed and compared. In an aspect, the MD simulations provides solvent accessible surface area (SASA) of the catalytic amino acids, cavity volume, the distance between gating residues, and stability of the CALB structure for correlating structure/function relationship of CALB. In other aspects, information provided by the MD simulation assists in the determination of how an amino acid alteration affects the size of the catalytic cavity and accessibility of the catalytic triad which ultimately affects the activity of CALB.

The methods provided herein show that the MD simulations based on the novel approach of performing MD simulation in first the implicit solvent followed by MD simulation in the explicit solvent are useful for investigating structure/function relationship of CALB and its variants. Amino acid residues can be accurately predicted for mutagenesis based on the results from the simulations. The methods provided herein allows the accurate identification of specific amino acid sites for alteration and the production of other CALB variants with improved synthesis activity.

Further, the expression systems for CALB provided herein enables the experimental validation of the mutants obtained based on the data obtained by the simulations.

The following examples illustrate exemplary methods provided herein. These examples are not intended, nor are they to be construed, as limiting the scope of the disclosure. It will be clear that the methods can be practiced otherwise than as particularly described herein. Numerous modifications and variations are possible in view of the teachings herein and, therefore, are within the scope of the disclosure.

EXAMPLES

Example 1

Expression of CALB and Variants in a Prokaryotic Host

An expression system for the eukaryotic enzyme CALB was developed and optimized in a *Bacillus subtilis* host. The lipase is expressed well under a variety of conditions, and in a relatively simple and inexpensive media. Factors that impact lipase expression in the system include growth temperature, nitrogen source and content, the presence of a non-hydrolyzable surfactant, and the biomass density of the inoculum. Surprisingly, the presence of a carbohydrate carbon source or dense inoculum reduces lipase expression/activity.

The secreted lipase is readily isolated from the culture supernatant by absorption and retains synthesis activity. It is possible to concentrate the media by ultrafiltration and retain >90% of the lipase activity, suggesting that a concentrated enzyme solution is feasible for commercially relevant biocatalyst production. Other options for improving expression include replacing the Pgrac inducible promoter with a strong constitutive promoter that is active after the culture enters stationary phase. Fed batch or chemostat culture conditions can also be used to maintain the culture in the optimum growth phase for enzyme production.

Detecting CALB Lipase Expression in *Bacillus Subtilis*

The native *Candida antarctica* lipase B (CALB) coding region was codon-optimized for yeast, synthesized, and cloned as a translation fusion into the pHT43 expression vector (FIG. 1). The *Bacillus subtilis* host strain WB800N (MoBiTec) was used throughout. Genotype: trpC2 (Trp−) nprE aprE epr bpr mpr::ble nprB::bsr .vpr wprA::hyg cm:: neo; NeoR Secreted lipase expression in *Bacillus subtilis* was verified on plates and in liquid culture. On plates, cells expressing an active lipase (CALB) grew and generated a zone of clearing when plated on a thin overlay of an opaque ester emulsion. Suitable indicator esters for reporting lipase activity include medium chain triglycerides (MCT), octyl octanoate (1%) and Tween 80 (0.1 to 1%) added to solid media (LB agar, 50 mM phosphate buffer pH 7, 6 mg/L chloramphenicol). In vector pHT43, it is necessary to induce protein expression from the construct with IPTG, at 0.5 to 1 mM (or 25 ul per plate of 100 mg/ml IPTG added to cells before plating).

Optimization of Inducible CALB Lipase Expression in *Bacillus Subtilis*

In a series of experiments, a WT CALB lipase expression construct 22, which is sequence-identical to the mature native CALB, was expressed in *Bacillus subtilis*. The inoculum, growth media and induction regime were varied. When LB agar (LBA) is indicated in the inoculum column, the inoculum was a cell suspension made from a bacterial lawn grown on solid media overnight. The inoculated liquid cultures were allowed to grow 2-6 h (155 rpm, 37° C., baffled flask) before lipase expression was induced with the addition of 1 mM IPTG. The cells were separated from the expression medium 20-26 h post induction by centrifugation (10 min., 10,000×g, 10° C.). Soluble lipase in the culture supernatant was adsorbed to the resin as described. The initial esterification reaction used a 10% enzyme loading (100 mg dry resin for 1 g of reactant mix; a 1:1 molar ratio of 2-ethylhexanol:oleic acid), stirred in a closed vial at 55° C., 800 rpm. Active enzyme preparations were also analyzed in reactions at lower enzyme loadings (5% and 2% resin). The reaction mix was analyzed by GC, and 2-ethylhexyl oleate (EHO) formation was estimated as peak area %.

A review of the results in Table 1.1 suggests that including the non-hydrolyzable surfactant Pluronic L61 at 0.1% and buffering the media at pH 7 with 50 mM phosphate buffer for the inoculum and optionally for the expression media leads to the highest lipase activity (Rows 1, 8-11). Surprisingly, glycerol as a supplemental carbon source at 2 or 0.5% did not promote lipase expression (Rows 3, 4, 13, 15, 17). Addition of other surfactants or esters to either the inoculum or the expression medium had no apparent benefit. A buffered growth medium containing 1% yeast extract and 1% tryptone (YT) gave slightly better results than LB (0.5% yeast extract, 1% tryptone, 1% NaCl) routinely used for propagation of *E. coli* and Bsub (Row 16 vs 12). Media containing 1% yeast extract and 1% casamino acids (YC) was also suitable for lipase expression (Rows 14 & 18).

TABLE 1.1

Survey of growth conditions for inducible lipase expression in *Bacillus subtilis*

| Row | Inoculum | Growth media | Induced at | Grown for | ml/g resin | % EHO at 24 h, resin loading 10% | 5% |
|---|---|---|---|---|---|---|---|
| 1 | LBA chlor6 + 50 mM PO4 + 0.1% L61 | LB chlor6 + 0.1% L61 | 4 h | 24 h | 20 | 72 | 50 |
| 2 | LBA chlor6 + 50 mM PO4 + 0.1% L61 | LB chlor6 + 0.1% L61 + 25 mM oct-oct | 4 h | 24 h | 20 | 59 | |
| 3 | LBA chlor6 + 50 mM PO4 + 0.1% L61 | LB chlor6 + 0.1% L61 + 2% glycerol | 4 h | 24 h | 20 | 16 | |
| 4 | LBA chlor6 + 50 mM PO4 + 0.1% L61 | LB chlor6 + 0.1% L61 + 2% glycerol + 25 mM oct-oct | 4 h | 24 h | 20 | 13 | |
| 5 | LB chlor6 (overnight culture) | LB chlor6 + 0.1% L61 | 6 h | 20 h | 26 | 71 | 52 |
| 6 | LB chlor6 (overnight culture) | LB chlor6 + 0.1% L61 + 25 mM oct-oct | 6 h | 20 h | 26 | 29 | |
| 7 | LBA chlor6 | LB chlor6 + 0.1% L61 | 2 h | 22 h | 28 | 24 | |
| 8 | LBA chlor6 + 50 mM PO4 + 0.1% L61 | LB chlor6 + 0.1% L61 | 2 h | 22 h | 28 | 79 | 64 |
| 9 | LBA chlor6 + 50 mM PO4 + 0.1% Tween80 + 25 mM oct-oct | LB chlor6 + 0.1% L61 | 2 h | 22 h | 28 | 74 | |
| 10 | LBA chlor6 + 50 mM PO4 + 0.1% L61 + 0.1% Tween80 + 25 mM oct-oct | LB chlor6 + 0.1% L61 | 2 h | 22 h | 28 | 76 | |
| 11 | LBA chlor6 + 50 mM PO4 + 0.1% L61 | LB chlor6 + 0.1% L61 + 50 mM PO4 | 2 h | 22 h | 28 | 79 | 56 |
| 12 | LBA chlor6 + 50 mM PO4 + 0.1% L61 | LB chlor6 + 0.1% L61 + 50 mM PO4 | 4 h | 20 h | 26 | | 61 |
| 13 | LBA chlor6 + 50 mM PO4 + 0.1% L61 | LB chlor6 + 0.1% L61 + 50 mM PO4 + 0.5% glycerol | 4 h | 20 h | 26 | | 42 |
| 14 | LBA chlor6 + 50 mM PO4 + 0.1% L61 | YC chlor6 + 0.1% L61 + 50 mM PO4 | 4 h | 20 h | 26 | | 68 |
| 15 | LBA chlor6 + 50 mM PO4 + 0.1% L61 | YC chlor6 + 0.1% L61 + 50 mM PO4 + 0.5% glycerol | 4 h | 20 h | 26 | | 19 |
| 16 | LBA chlor6 + 50 mM PO4 + 0.1% L61 | YT chlor6 + 0.1% L61 + 50 mM PO4 | 4 h | 20 h | 26 | | 73 |
| 17 | LBA chlor6 + 50 mM PO4 + 0.1% L61 | YT chlor6 + 0.1% L61 + 50 mM PO4 + 0.5% glycerol | 4 h | 20 h | 26 | | 65 |
| 18 | LBA chlor6 + 50 mM PO4 + 0.1% L61 | YC chlor6 + 0.1% L61 + 50 mM PO4 | 4 h | 20 h | 25 | | 66 |
| 19 | LBA chlor6 + 50 mM PO4 + 0.1% L61 | YC chlor6 + 0.1% L61 + 50 mM PO4 + 100 mg/L tryptophan | 4 h | 20 h | 25 | | 65 |

Constitutive Expression of CALB Lipase in *Bacillus Subtilis*

Changes to the pHT43 expression vector were made to simplify lipase expression. In the pHT43 vector, expression of the target gene (lipase) is controlled by the Pgrac promoter. Pgrac is an artificial promoter consisting of *Bacillus subtilis* groE promoter, lac operator and gsiB ribosome binding site. This is a strong IPTG-inducible promoter for *Bacillus subtilis*. Pgrac is repressed by the lacI repressor encoded on the pHT43 plasmid vector, and requires induction by the lactose analog IPTG. To allow constitutive lipase expression in *Bacillus subtilis*, the lacI repressor was deleted from the construct using existing restriction sites SnaBI and SfoI. The pHT43 expression vector (MobiTec) was modified for constitutive protein expression by deleting the laqI repressor encoded on the vector to generate pHT43D. The 1.1 kb SnaBI/SfoI fragment containing the laqI gene in pHT43 was deleted and confirmed by PCR. The repressor deletion expression constructs in pHT43D were readily propagated in *B. subtilis* with no obvious growth impairment, and the lipase was expressed constitutively from the Pgrac promoter without the need for IPTG induction. The lacI deletion construct could be propagated in *E. coli* strains that contain an episomal copy of the lacI repressor. The lacI repressor was deleted from a construct expressing the native CALB sequence (strain 22) and verified by restriction mapping. The lacI deletion construct containing the native CALB coding region (22Δ) was transformed into *Bacillus subtilis*.

The repressor deletion WT lipase construct (22Δ) was expressed in *Bacillus subtilis* and compared to the original lipase construct (22). The culture with the repressor deletion construct (22Δ) was uninduced, while the culture with the original construct 22 was induced with 1 mM IPTG at 2 h. In both cases, the inoculum was a cell suspension made from a lawn of the strain grown on LB agar+50 mM phosphate buffer, pH 7.0 and 0.1% Pluronic L61. After a total of 24 h of growth, lipase in the culture supernatant was immobilized on resin (1 g Lewatit VP OC1600 resin/25 ml media) and 2-ethylhexyl oleate (EHO) esterification reactions were performed as described previously. Results of the optimization of lipase expression in the repressor deletion construct are summarized in Table 1.2. The repressor deletion construct resulted in lipase expression identical to that obtained from the original construct after induction by 1 mM IPTG. The lacI deletion vector was a great improvement over the inducible system because it eliminates a process step, and the inducer IPTG is a costly and hazardous reagent.

TABLE 1.2

Lipase activity expressed from the expression construct with the lacI repressor (22) and without (22Δ).

| Expression construct (NB p. 100, 104) | Relative activity (% EHO at 24 h 2% resin) |
|---|---|
| 22, 1 mM IPTG @ 2 h | 100% |
| 22Δ (n = 6) uninduced | 97-104 |

Conditions: 1% Yeast extract; 1% Tryptone; 50 mM phosphate buffer pH 7 (Hydrion). Sterile filter; add 0.1% Pluronic L61 and 6 mg/L chloramphenicol. Inoculate and grow 24 h (37 deg C., 160 rpm). Immobilize: 25 ml culture supernatant/g resin.

Optimizing Growth Media for CALB Expression in *Bacillus*

Focusing on the constitutive WT CALB expression construct with the lacI deletion (22Δ), growth conditions for the expression culture were investigated. The standard media recipe contains only two nutrient sources: yeast extract and tryptone (an enzymatic digest of casein, a milk protein), plus phosphate buffer, antibiotic and non-hydrolyzable surfactant. The relative amounts of each nutrient were varied, and the pre-mixed phosphate buffer preparation was replaced with its individual components. The growth temperature was also varied. Table 1.3 summarizes the results of the growth conditions on relative lipase esterification activity.

Surprisingly, addition of the carbon sources glycerol (Table 1.1) or glucose (Table 1.3) to the media reduced lipase expression or activity. An inverse relationship between cell biomass and lipase activity is evident when the inoculum density is increased (Table 1.3), with a higher biomass inoculum leading to lower lipase expression/activity. Reducing tryptone to 0.5% or eliminating yeast extract reduced the lipase expression/activity, as did changing the temperature from 37° C. Reducing the yeast extract content to 0.5% had no impact on lipase activity, but would reduce the cost of the media.

TABLE 1.3

Media and temperature effects on lipase activity from 22Δ

| Row | Media/growth condition change* | Relative synthesis activity (% EHO at 24 h, 2% resin) |
|---|---|---|
| 1 | Standard conditions* | 100% |
| 2 | Substitute Pluronic L31 for L61 | 117 |
| 3 | Substitute Pluronic L35 for L61 | 99-121 |
| 4 | Substitute Pluronic F68 for L61 | 104 |
| 5 | 10 mM calcium nitrate | 93 |
| 6 | 10 mM magnesium sulfate | 103 |
| 7 | Glucose, 1% | 65 |
| 8 | Glucose 1%, Sodium citrate 1%, MgSO4 10 mM | 85 |
| 9 | Standard inoculum | 100 |
| 10 | 2X inoculum | 65 |
| 11 | 5X inoculum | 48 |
| 12 | 1% Yeast extract, 1% Tryptone | 100 |
| 13 | 0.5% Yeast extract, 0.5% Tryptone | 74 |
| 14 | 0.5% Yeast extract, 1% Tryptone | 103 |
| 15 | 0.2% Yeast extract, 1% Tryptone | 90 |
| 16 | 0% Yeast extract, 1% Tryptone | 75 |
| 17 | Grow liquid culture at 37° C. | 100 |
| 18 | Grow liquid culture at 30° C. | 80 |
| 19 | Grow liquid culture at 42° C. | 62 |

*Standard conditions: Expression media: 1% Yeast extract; 1% Tryptone; 50 mM phosphate buffer pH 7 (Hydrion). Sterile filter; add 0.1% Pluronic L61 and 6 mg/L chloramphenicol. Inoculate using a cell suspension from a lawn grown on solid media (LBA chlor6 + 50 mM PO4 + 0.1% L61) and grow 24 h (37° C., 160 rpm). Immobilize: 25 ml culture supernatant/g resin.

Concentrating *Bacillus Subtilis*-Expressed Lipase Activity

Commercial enzyme solutions are typically concentrated, such as by precipitation or chromatography, and stabilized prior to distribution. On large scale, ultrafiltration can be used to concentrate an enzyme solution through a filter with a molecular weight cut-off smaller than the size of the enzyme. In theory, if the *Bacillus subtilis* culture supernatant containing the secreted lipase can be concentrated, then the immobilized activity on a resin dry weight basis can be increased. A 50 ml culture of *Bacillus subtilis* constitutively expressing CALB (22Δ) was grown using the standard conditions. After 24 h, 25 ml of culture supernatant was used directly for immobilization, as for the standard protocol. The other 25 ml was first cleared through a 0.2 um filter to remove any cells, then concentrated to a final volume of 2 ml through a 10,000 MW cutoff PES filter (Corning Spin-X UF 20, 7500×g, 15° C., 80 minutes). The concentrate was diluted in water to 25 ml before adding resin. The culture supernatant concentrate retained 91% of the lipase activity, while the filtrate had no activity above background.

Example 2

Comparison of Native CALB Structure in Implicit and Explicit Solvent

In this Example, MD simulations are used to study the CALB variants that are already isolated.

This Example include a comparison between newly developed methods (case 3) and conventional methods (case 1 and case 2). See FIGS. 2A and 2B.

Implicit aqueous solvent models can represent the protein structure in an aqueous environment. For implicit solvents (case 2 and case 3), all starting structures (wild type, 529 and 554) were subjected to 10,000 steps minimization followed by heating the system to 300 K in 100 ps using Langevin thermostat. The MD simulations were carried out for 12 ns and temperature was maintained at 300 K with Berendsen thermostat.

Explicit solvent models (case 1 and case 3) represents the protein structure in an environment that mimics the esterification reaction mix (3:1:1:1 molar ratio of octanol:octanoic acid:2-ethylhexanoic acid:benzoic acid). All solvent structures (octanol, octanoic acid, 2-ehtylhexanoic acid, and benzoic acid) were made by Discovery Studio Visualizer 4.0 and their partial charges were obtained using Antechamber with AM1-BCC method in AMBER 12 package. The solvent box (3:1:1:1 reaction mix) for each variant were made via Xleap in Ambertools. As a starting structure in explicit solvent, all CALB (wild type, 529, 554) were extracted from a last frame of simulations using implicit solvent model and solvated into aforementioned solvent box. In all cases, the systems were carefully minimized and an equilibrated by 11 stages starting from minimization for 10,000 steps while CALB was restrained for 200 kcal/mol. In the same restrained state, temperature was gradually increased to 300 K in 40 ps. A short NPT MD simulation was performed for 200 ps under the 200 kcal/mol constraint on CALB. Then another minimization for 10,000 steps followed with 20 kcal/mol restraint on CALB. Additional short NPT simulation was carried out for 20 ps with same constraint energy. Four consecutive minimization stages were performed for 1,000 steps by gradually decreasing constraint of CALB from 20 kcal/mol to 0 kcal/mol. As a final equilibration step, the system was reheated to 300 K without any constraints of CALB for 40 ps, respectively. After careful minimization and equilibration steps, production MD runs were performed under the NPT-ensemble for 60 ns at 300 K, 1 atm.

Figure 2B:
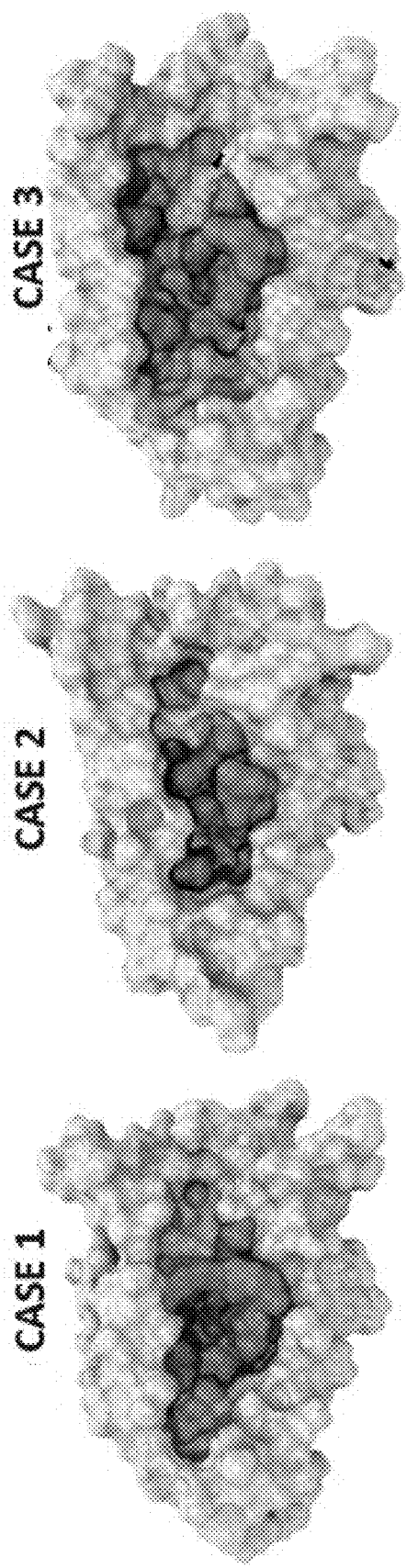

As shown in FIGS. 2A and 2B, the structure of Variant 554 changed as a function of the method used. In case 1, where variant 554 was only simulated in explicit solvent (reaction mixture), no significant structural changes near the catalytic cavity were observed and entire structure was almost identical to the wild type. In case 2, where variant 554 was simulated in only aqueous solution, conformational changes near catalytic cavity resulted in narrower cavity entrance with strong interactions between E188D and L278. In case 3, when MD simulations followed the experimental procedures, Variant 554 showed a wide open cavity entrance and high solvent accessible surface area of catalytic triad. This serves as an example illustrating that key mutation sites for better enzyme activity, such as E188D can be overlooked if conventional simulation approaches (using only water or organic solvents as a solvent) were used in this study.

Example 3

Isolation of Variant 529 with Two Amino Acid Changes (D223G, S227T) & Comparative Variants with Single Amino Acid Changes Only (D223G) or (S227T)

Random changes within 3 amino acids of the active site residues were targeted in the mature native CALB amino acid sequence. A very large pool of sequence variants was screened for an active lipase phenotype on plates containing an indicator ester. A single variant showed a significant increase in benzoic acid esterification: variant 529, with two amino acid changes from the native CALB sequence.

Figure 3:
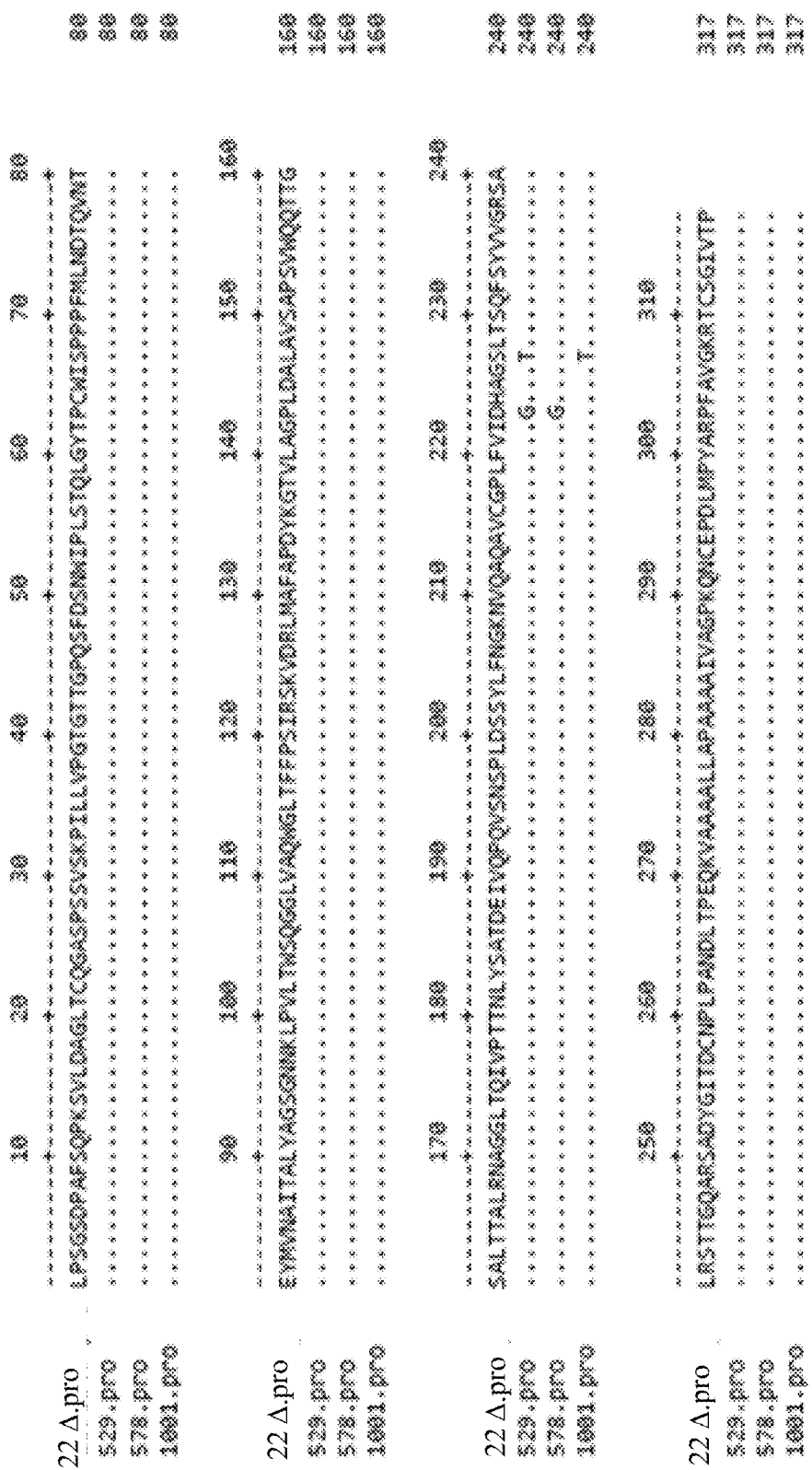
FIG. 3 shows the alignment of amino acid sequences of the native CALB sequence (22delta, SEQ ID NO: 2) with variants 529 (D223G and S227T), 578 (D223G, SEQ ID NO: 29), and 1001 (S227T, SEQ ID NO: 30).

FIG. 3 shows the amino acid sequences of CALB variants aligned with the native CALB sequence (22Δ). Variant 529 contains two residue changes (D223G and S227T) near the active site residue H224. Based on the sequence of variant 529, comparative variants were generated that contained only one amino acid change, either D223G (variant 578) or S227T (variant 1001) alone.

The variants were expressed in the *Bacillus subtilis* WB800N host grown at 25 ml scale, and immobilized for synthesis activity. The relative benzoic acid esterification activity (BZA) and the 2-ethylhexyl palmitate synthesis activity (2-EHP) were compared between native and variant expressed sequences. The synthesis activity of variant 529 with two amino acid substitutions is greater than either single amino acid substitution.

| Variant | Screening activity, BZA | Screening activity, 2-EHP |
|---|---|---|
| Empty vector | 0 | 4 |
| WT (22Δ) | 1.0 | 10 |
| 1001 | 2.4 | 18 |
| 578 | 2.5 | 19 |
| 529 | 3.0 | 24 |

BZA Esterification Activity: The standard benzoic acid (BZA) synthesis screening reaction mix contained 3 mole equivalents of octanol, and 1 equivalent each of octanoic acid, 2-ethylhexanoic acid and benzoic acid. Dry resin (50 mg) was weighed into a 3 dram glass vial, and 1 g of reaction mix was added along with a stir bar. The reactions were stirred (800 rpm) at 55° C. for 24 h, then 25 ul was sampled into 1 ml of methanol for analysis by GC. Relative conversion was estimated by integrating only the octanol and three ester peaks. Total esterification was expressed as the % peak area of the combined esters to the total peak area, while the esterification of 2-ethylhexanoic acid and benzoic acid was expressed relative to octanoic acid (ester peak areas only).

The plasmid from variants 529, 578, and 1001 was isolated and re-transformed into the *Bacillus subtilis* WB800N host. At least 4 independent colonies were expressed in cultures at 25 ml scale, and immobilized separately for synthesis activity. The benzoic acid esterification activity (BZA) and the 2-ethylhexyl palmitate synthesis activity (2-EHP) were compared. The synthesis activity of variant 529 with two amino acid substitutions is consistent among multiple independent transformants and greater than either single amino acid substitution.

| Variant | Avg Synthesis Activity BZA (n) |
|---|---|
| 1001 | 2.0 (4) |
| 578 | 2.6 (6) |
| 529 | 3.4 (8) |

Methods: The template for mutagenic PCR was a WT CALB coding region cloned into the modified pHT43Δ vector. Vector primers 2619_F and 2990_R were used along with the appropriate mutagenic primers to generate the short overlapping fragments containing the targeted amino acid changes, using Taq DNA polymerase (NEB). Fragments were amplified using internal and vector primer pairs. The pHT43Δ vector fragment (with the laqI deletion for constitutive expression) was amplified with primers (SIGSEQ_R and G341_F) using a high-fidelity polymerase blend (LongAmp Taq, NEB) to generate a linear vector fragment that included a sequence that overlapped the sequence-modified lipase gene fragments. Then the vector and insert fragments were combined in a multimerization reaction (LongAmp Taq, no added primers), in which the overlapping ends of the vector and insert fragments served to prime the extension reaction, creating long linear repeats of alternating insert and vector. These multimers appeared as very high molecular weight DNA on an agarose gel and could be used to transform B. subtilis directly.

| Primer sequences, 5' to 3' | |
|---|---|
| 2619_F | GCTTGGTACCAGCTATTGTAACATAATCG (SEQ ID NO: 23) |
| 2990_R | CAGACAAAGATCTCCATGGACGCGTG (SEQ ID NO: 24) |
| G341_F | GGTAAGAGAACTTGTTCTGGTATTGTTACTCCATAATA ACCC (SEQ ID NO: 25) |
| SIGSEQ_R | CAGCGTGCACATAAGCACAAGTCTGAACGAAACTGTCC GC (SEQ ID NO: 26) |

The PCR-assembled multimers were effective for direct transformation of B. subtilis competent cells, strain WB800N, and selected on plates containing chloramphenicol and an indicator ester to visualize colonies expressing a hydrolytically active lipase. Indicator plates contained LB agar, 50 mM phosphate buffer pH 7.0, 6 mg/L chloramphenicol, 0.2% Tween 80, and 0.05% PEG6000 distearate. Active lipase appeared as a white or opaque halo surrounding a colony. Plasmid was isolated from any leads strains and the lipase gene amplified from the vector using primers pHT2619_F and pHT2990_R. The 1.2 kb fragment was G-50 column purified and submitted for sequencing with the amplification primers (Eurofins MWG Operon). The DNA sequences were analyzed (trimmed, translated and aligned) using the programs in the DNASTAR core suite.

For lipase expression and immobilization at 25 ml scale, colonies were picked into a small volume of Expression Media, and the cell suspension was first plated on L61 plates (LB agar, 50 mM phosphate buffer pH 7.0, 0.1% Pluronic L61, 6 mg/L chloramphenicol) and incubated overnight at 37° C. Expression Media (~2 ml) was added to the plate surface and the cells scraped off to create a dense cell suspension. This cell suspension was used to inoculate 25 ml of expression media. After 24 h of growth (37° C., 160 rpm), the cells were pelleted by centrifugation (10 min, 10,000×g, 10° C.), and the supernatant was decanted to an 8-dram glass vial. To immobilize the lipase from the cleared broth, 0.85 g of resin (Purolite Lifetech™ ECR 1030M) was added to each vial, and the vials were rotated horizontally overnight at room temperature. The resin was transferred to a paper filter and rinsed twice with water. The resin was air-dried, and used in synthesis reactions to determine relative synthesis activity.

The standard benzoic acid (BZA) synthesis screening reaction mix contained 3 mole equivalents of octanol, and 1 equivalent each of octanoic acid, 2-ethylhexanoic acid and benzoic acid. Dry resin (50 mg) was weighed into a 3 dram glass vial, and 1 g of reaction mix was added along with a stir bar. The reactions were stirred (800 rpm) at 55° C. for 24 h, then 25 ul was sampled into 1 ml of methanol for analysis by GC. Relative conversion was estimated by integrating only the octanol and three ester peaks. Total esterification was expressed as the % peak area of the combined esters to the total peak area, while the esterification of 2-ethylhexanoic acid and benzoic acid was expressed relative to octanoic acid (ester peak areas only).

The 2-ethylhexyl palmitate (2-EHP) reaction contained 5 grams of palmitic acid and 2.5 grams of 2-ethylhexanol and 50 mg of dry resin. The reactants were melted at 72° C. for 15 minutes, then the reaction proceeded at 72° C. for 4 h with stirring, then 25 ul was sampled into 1 ml of methanol for analysis by GC.

GC Analysis: Analyzed on an Agilent 6890 GC using an Agilent DB-5 column (#122-5032; 30m×0.25 mm×0.25 uM) with flame ionization detection and split injection with 2 uL injection volume. Temperature program: 100° C. for 10 min, then 100-250° C. at a rate of 25° C./min, hold at 250° C. for 9 min.

Example 4

Explicit Solvent Model of Variant 529 and Identification of E188 as a Target for Variation A crystal structure of CALB was obtained from Protein Data Bank (PDB, Code: 1TCA) and mutations of amino acids were introduced via Discovery Studio Visualizer 4.0 software (Accelrys, USA) (Discovery Studio Modeling Environment, (2007) Accelrys Software Inc., San Diego). In Variant 529, two amino acids, D223 and S227, were replaced with Glycine and Threonine, respectively. Two CALB structures, wild type (WT) and Variant 529 were solvated into implicit solvent, which represents the protein structure in an aqueous environment and simulated for 12 ns. The resultant structures of the wild type and Variant 529 were solvated with explicit reaction mixtures which is considered identical reaction media as used in aforementioned experiments. Then MD simulations in explicit reaction media were performed for 100 ns to refine the structure of the wild type and 529 variant in a reaction mix. AMBER 12 with FF12SB (for proteins) and GAFF (for reaction mixtures) force fields was used for MD simulations.

TABLE 4.1

Summary of structural analysis of WT and Variant 529 after MD refinement with implicit aqueous solvent and explicit reaction mixture.

| Variant | Cavity volume ($Å^3$) | Solvent accessible surface area ($Å^2$) | | | Enzyme activity (Ratio to WT) |
|---|---|---|---|---|---|
| | | SER-105 | ASP-187 | HIS-224 | |
| WT | 356.8 | 5.45 (±1.23) | 0.00 (±0.01) | 4.87 (±2.05) | 1.0 |
| 529 | 490.5 | 6.73 (±6.25) | 0.01 (±0.03) | 17.91 (±7.90) | 3.5 |

Since reaction mixtures in this study were directly used as substrates for synthesis reactions, cavity volume and solvent accessibility of catalytic triad can be important factors for enzyme activity.

From the refined 3-D structure of two cases, the volume of catalytic cavity was measured via Caver catalyst software. As shown in Table 4.1, Variant 529 has a larger cavity volume (356.8 $Å^3$) as compared to the cavity volume of WT (490.5 $Å^3$).

Solvent accessible surface area (SASA) was defined as the surface area of molecules that is accessible to solvent molecules and the SASA of the catalytic triad residues was calculated through GETAREA (University of Texas Medical Branch, USA). Simulation results showed that SASA of H224 in Variant 529 case was approximately 4-fold greater than that of the WT.

A larger cavity volume and higher SASA of catalytic triad residues illustrated that the catalytic triad of Variant 529 has a higher chance to interact with solvent molecules in the reaction mixture thus leading to greater enzyme activity as compared to WT.

Figure 4B:
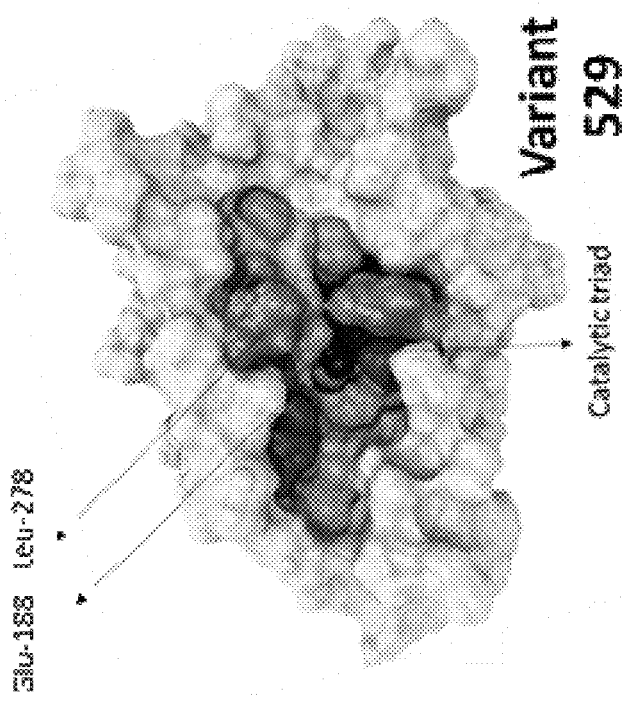
FIGS. 4A and 4B show final simulation snapshots after MD refinement of WT and 529 structure.
Figure 4A:
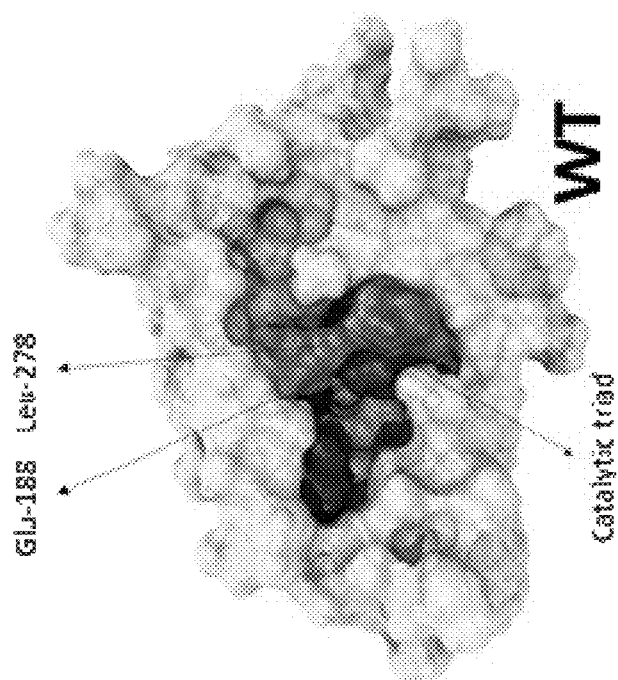

Final simulation snapshots indicated that two amino acids, E188 and L278 tend to interact with each other in WT case but this interaction was partially broken in Variant 529 which resulted in the exposure of catalytic triad to the solvent as well as made a larger cavity volume (FIGS. 4A and 4B). In both cases, E188 and L278 acted as the gate residues: closed cavity conformations in WT case and open cavity structures in Variant 529. The interactions between E188 and L278 and its conformations were quantified via analysis of the average distance between center of mass (COM) of two residues (Table 4.2). This analysis was performed by CPPTRAJ module in AMBER 12 package and the last 10 ns of simulation trajectories were used for obtaining average distance between these residues with the standard deviations. As a reference, the same analysis was performed for CALB the crystal structure. Even though an open cavity structure was observed in Variant 529, it was found that two catalytic residues, H224 and D187 were structurally screened by E188. Also L278 can frequently interact with E188 during the simulation of Variant 529 forming a closed cavity conformation. For these reasons, E188 was selected as a target for the variation.

TABLE 4.2

The relation between catalytic gate opening and distance between E188 and L278 amino acids.

| Case | Distance between COM of 188 and 278 (with a standard deviation) (Å) | Gate structure |
|---|---|---|
| Crystal CALB | 8.77 (n/a) | Closed |
| WT | 8.54 (±0.61) | Closed |
| 529 | 9.96 (±1.07) | Open |

Example 5

Isolation of Variant 554 (E188D, D223G, S227T)

Position E188 was predicted to be a good candidate for change based on the structural models in Example 4. This residue was allowed to vary to any amino acid using degenerate primers. Only lipase variants with a further E188D change resulted in an increase in synthesis activity over the parent variant 529.

Variant 554 was expressed in the *Bacillus subtilis* WB800N host grown at 25 ml scale, and immobilized for synthesis activity. The relative benzoic acid esterification activity (BZA) and the 2-ethylhexyl palmitate synthesis activity (2-EHP) were compared between native and variant expressed sequences. The synthesis activity of variant 554 with three amino acid substitutions is greater than the parent sequence with two amino acid changes.

| Variant | Screening activity (BZA) | 2-EHP |
|---|---|---|
| Empty vector | 0 | 4 |
| WT (22Δ) | 1.0 | 10 |
| 529 | 3.0 | 24 |
| 554 | 6.0 | 33 |

The plasmid from variant 554 was isolated and re-transformed into the *Bacillus subtilis* WB800N host. At least 4 independent colonies were expressed in cultures at 25 ml scale, and immobilized separately for synthesis activity. The benzoic acid esterification activity (BZA) was determined. The synthesis activity of variant 529 with two amino acid substitutions is consistent among multiple independent transformants and greater than either single amino acid substitution.

| Variant | Avg BZA (n) |
|---|---|
| 554 | 5.7 (8) |

Cloning, expression and analysis were performed as in Example 3. The template for mutagenic PCR was variant 529. Fragments were amplified using primer pairs (E222X_F plus 2990R) and (2619_F plus L233wt_R), where E188 was varied to any amino acid. The pHT43Δ vector fragment was amplified with primers (SIGSEQ_R and G341_F) using a high-fidelity polymerase blend (LongAmp Taq, NEB) to generate a linear vector fragment that included a sequence that overlapped the sequence-modified lipase gene fragments. Then the vector and insert fragments were combined in a multimerization reaction with no added primers, and used to transform *B. subtilis* WB800N directly.

```
Primer sequences, 5' to 3'
E222X_F    GTATTCTGCCACCGATNNNATCGTCCAACCACAAGTTT
           CT (SEQ ID NO: 27)

L233wt_R   CCATTAAACAAGTAAGAAGAATCCAATGGAGAGTTAG
           (SEQ ID NO: 28)
```

Example 6

Explicit Solvent Model of Variant 554 with Analyses

Additional E188D mutation in the Variant 529 background (Variant 554) was employed via Discovery Studio Visualizer 4.0 software (Discovery Studio Modeling Environment, (2007) Accelrys Software Inc., San Diego). The same simulation procedures described in Example 2 (case 3) were used: MD simulation in implicit solvent condition for 12 ns followed by additional MD simulation in explicit reaction mixtures for 100 ns were used for the structure refinement of Variant 554. As stated in Example 5, E188 was chosen as a next target for the mutation because it can block the accessibility of catalytic triad to the solvent as well as frequently interact with L278 forming closed cavity conformations. Since stability of the positively charged catalytic residue H224 can be strongly affected by charged neighbors, a negatively charged residue near H224, E188, was replaced with a smaller but negatively charged residue, Asp (D).

Figure 5:
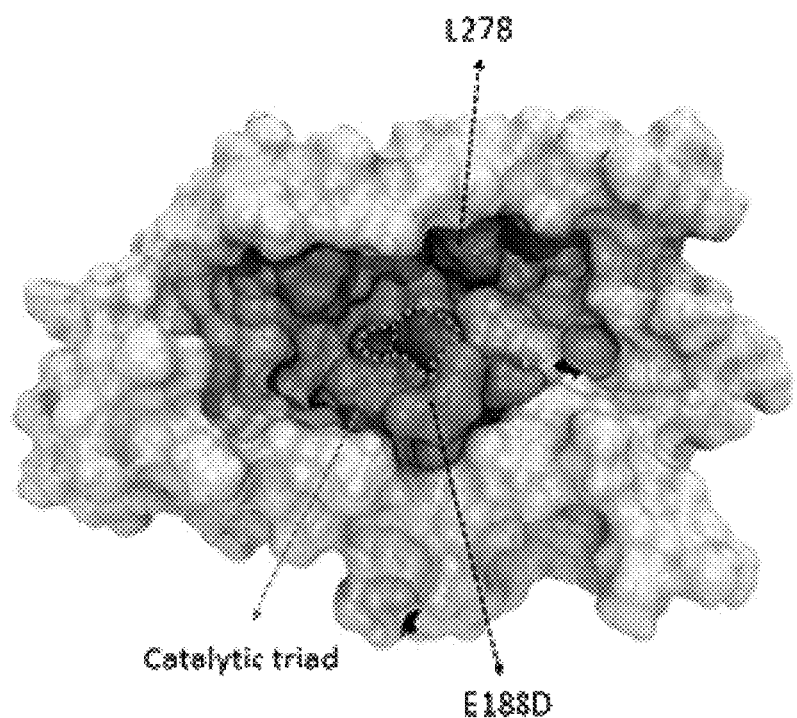
FIG. 5 shows final simulation snapshot of Variant 554. Dotted line is drawn around the catalytic triad.

Varying E188 to D caused a wide-open catalytic cavity with a completely exposed catalytic triad (FIG. 5). These significant structural changes resulted in approximately 7-fold higher SASA of catalytic triad and a 2-fold larger cavity volume of Variant 554 as compared to those of WT CALB (Table 6.1). In Variant 529, the interactions between E188 and L278 were the key factor for open cavity conformation as well as were directly related to the enzyme activity. Since E188 was replaced with the smaller residue in Variant 554, the interaction between D188 and L278 became weaker than that between E188 and L278 in Variant 529. This weak interaction led to a complete separation between these residues with larger distance (Table 6.2) and, therefore, L278 became buried in the enzyme structure due to its hydrophobicity. Analysis of the simulations for other variants indicated a strong correlation between activity and open gate structure or large distance between 188 and 278 (Table 6.2).

TABLE 6.1

Assessment of structural differences between WT and Variant 554.

| Variant | Cavity volume (Å$^3$) | Solvent accessible surface area (Å$^2$) | | | Enzyme activity (Ratio to WT) |
|---|---|---|---|---|---|
| | | SER-105 | ASP-187 | HIS-224 | |
| WT | 356.8 | 5.45 (±1.23) | 0.00 (±0.01) | 4.87 (±2.05) | 1.0 |
| 554 | 612.6 | 5.51 (±3.60) | 1.92 (±1.36) | 33.25 (±8.98) | 5.9 |

TABLE 6.2

The relation between catalytic gate opening and distance between E188 and L278 amino acids.

| Variant | Distance between 188 and 278 (with a standard deviation) (Å) | Enzyme Activity (Ratio to WT) | Gate Structure |
|---|---|---|---|
| 569 | 4.30 (±0.92) | <1 | Closed |
| WT | 5.22 (±0.94) | 1 | Closed |
| 551 | 7.35 (±0.91) | 2.5 | Open/Closed |
| 529 | 9.48 (±1.13) | 3.0 | Open |
| 554 | 10.63 (±1.06) | 5.9 | Open |
| 953 | 10.13 (±0.79) | 10.0 | Open |

Example 7

Octyl Octanoate Synthesis Kinetics of WT, 578, 529, 554

WT CALB and lipase variants 578, 529 and 554 were expressed in *Bacillus subtilis* as described in Example 3, and the secreted lipase was adsorbed from the broth onto Purolite™ ECR1030M resin. The dried resin was used in synthesis reactions to compare the synthesis activities of the different lipase sequences.

The following were added to a 3 dram glass vial: stir bar, X grams 1-octanol (see table below) and Y grams octanoic acid (see Table 7.1). Each reaction condition (A,B,C,D) was prepared in triplicate. Vials were stirred and maintained at reaction temperature of 60° C. for 15 minutes.

TABLE 7.1

Reactant mixtures - various equivalent ratios of 1-octanol & octanoic acid

| Reaction | Mole Equivalents 1-Octanol | Mole Equivalents Octanoic acid | mmol 1-Octanol | X = g 1-Octanol | mmol 1-Octanoic acid | Y = g 1-Octanoic acid |
|---|---|---|---|---|---|---|
| A | 1 | 2 | 3.51 | 0.46 | 7.02 | 1.01 |
| B | 1 | 1 | 3.50 | 0.46 | 3.50 | 0.5 |
| C | 2 | 1 | 7.02 | 0.91 | 3.51 | 0.51 |
| D | 3 | 1 | 10.54 | 1.37 | 3.51 | 0.51 |

Reactions were initiated by adding carefully pre-weighed dry resin with immobilized lipase (~30 mg each) into each reaction vial. Upon addition of lipase to each vial a stopwatch was immediately started. Vials were staggered in 30 second intervals to allow for consistent sampling. 50 µl was transferred from each vial to pre-weighed GC vials every 10 minutes for a total of 60 minutes for each reaction vial.

GC vials with added sample were then weighed and individual sample weights utilized to calculate micromoles octyl octanoate produced at each time point. A calibration curve was generated prior to reaction sampling using 2 mg/ml 1-methylnaphthalene in toluene as an internal standard. A calibration curve for octyl octanoate demonstrated linear response on the GC in the concentration range of 1.0 to 40.0 mg/ml octyl octanoate.

GC analysis: to each GC vial containing the above 50 µl sample were added 500 µl 2 mg/ml 1-methylnaphthalene (in toluene) as internal standard and 1000 µl toluene. Vials were capped and mixed by inversion. Each vial was analyzed on an Agilent 6890 gas chromatograph equipped with a 5% diphenyl/95% dimethyl polysiloxane capillary (20 m length, 0.25 mm ID, 0.25 µm film thickness, Restek RTX-5 Cat #10223-124) GC column and a flame ionization detector. Initial temperature was held at 100° C. for 3 minutes, then a gradient from 100° C. to 325° C. over 5.63 minutes. Temperature was held at 325° C. for 2.38 minutes for a final run time of 11.0 minutes.

Reaction rate of esterification was defined as micromoles octyl octanoate produced over time. The slope of each initial esterification rate (defined as reaction velocity) was divided by mg dry resin with immobilized lipase to yield a specific activity: micromoles octyl octanoate minute$^{-1}$ gram resin$^{-1}$. The initial synthesis rate of lipase variants 529 and 554 is 3.4 to 9.4 times greater than the WT lipase activity. The fastest rate was measured when the reactants were present in a 1:1 molar ratio.

| Micromoles octyl octanoate minute$^{-1}$ gram resin$^{-1}$ | | | | |
|---|---|---|---|---|
| | WT | 578 | 529 | 554 |
| A) 1:2 octanol:acid | | | | |
| Avg (st dev) | 100.2 (5.7) | 279.0 (17.7) | 343.7 (31.3) | 750.4 (53.1) |
| Ratio to WT | 1.0 | 2.8 | 3.4 | 7.5 |
| B) 1:1 octanol:acid | | | | |
| Avg (st dev) | 84.2 (6.0) | 320.6 (31.9) | 447.4 (47.2) | 794.1 (56.3) |
| Ratio to WT | 1.0 | 3.8 | 5.3 | 9.4 |
| C) 2:1 | | | | |

-continued

| Micromoles octyl octanoate minute$^{-1}$ gram resin$^{-1}$ | | | | |
|---|---|---|---|---|
| | WT | 578 | 529 | 554 |
| octanol:acid | | | | |
| Avg (st dev) | 92.1 (4.5) | 284.3 (2.4) | 412.7 (26.5) | 591.4 (8.6) |
| Ratio to WT | 1.0 | 3.1 | 4.5 | 6.4 |
| D) 3:1 octanol:acid | | | | |
| Avg (st dev) | 82.1 (5.6) | 232.9 (2.3) | 405.3 (3.9) | 580.9 (24.8) |
| Ratio to WT | 1.0 | 2.8 | 4.9 | 7.1 |

Example 8

2-ethylhexyl Palmitate Synthesis Kinetics of WT, 578, 529, 554

In a 50 ml conical tube, 50 mg of dry resin with immobilized lipase and 10 grams of Palmitic Acid were weighed into each tube, 1.03 equivalents (5.23 grams) of 2-Ethylhexanol was added. The tube was heated in 72° C. water bath for 45 minutes to melt all starting materials. Once melted each tube was placed in a heat block set at 72° C. A sparge needle was inserted into each tube through a vented cap to mix and nitrogen-strip the reaction. The sparge rate was set to 300 mL/min dry nitrogen for each tube.

Samples were taken at 0, 1 h, 2 h, 4 h, and 24 h and accurately weighed for analysis by a wt % GC method. GC analysis: Analyzed on a Hewlett-Packard 5890 GC equipped with a J&W DB-5 column, 30 m×0.25 mm with flame ionization detection and split injection with 2 uL injection volume. Temperature program: 100° C. for 9 min, then 100-300° C. at a rate of 25° C./min, hold at 300° C. for 10 min.

The initial rate of conversion (% palmitic acid converted/h) was determined from the slope of the data points from 0 to 4 h. The conversion rate relative to WT is also reported. Lipase variants with 2 (529) or 3 (554) amino acid changes have a 2-ethylhexyl palmitate synthesis rate 3.5 to 5.9-fold greater than WT CALB.

| | WT | 578 | 529 | 554 |
|---|---|---|---|---|
| % palmitic acid converted to ester (h-1) | 0.72 | 1.84 | 2.54 | 4.27 |
| r squared | 0.6 | 0.99 | 1 | 0.93 |
| ratio to WT | 1.0 | 2.6 | 3.5 | 5.9 |

Example 9

Octyl Octanamide Synthesis Kinetics of WT, 554

The following were added to a 3 dram glass vial: stir bar, 2.26 grams 1-octylamine and 2.77 grams methyl octanoate. Each reaction was performed in duplicate. Vials were stirred and maintained at reaction temperature of 60° C. for 15 minutes. A nitrogen sparge (250 ml/min) was used to remove the methanol by-product.

Reactions were initiated by adding carefully pre-weighed dry resin with immobilized lipase (~30 mg each) into each reaction vial. Upon addition of lipase to each vial a stopwatch was immediately started. Vials were staggered in 30 second intervals to allow for consistent sampling. 50 µl was transferred from each vial to pre-weighed GC vials every 30 minutes for a total of 180 minutes for each reaction vial.

GC vials with added sample were then weighed and individual sample weights utilized to calculate micromoles octyl octanamide produced at each time point. A calibration curve was generated prior to reaction sampling using 2 mg/ml 1-methylnaphthalene in toluene as an internal standard. A calibration curve for octyl octanoamide demonstrated linear response on the GC in the concentration range of 1.0 to 40.0 mg/ml octyl octanoamide.

GC analysis: to each GC vial containing the above 50 µl sample, added 500 µl 2 mg/ml 1-methylnaphthalene (in toluene) as internal standard and 1000 µl toluene. Vials were capped and mixed by inversion. Each vial was analyzed on an Agilent 6890 gas chromatograph equipped with a 5% diphenyl/95% dimethyl polysiloxane capillary (20 m length, 0.25 mm ID, 0.25 µm film thickness, Restek RTX-5 Cat #10223-124) GC column and a flame ionization detector. Initial temperature was held at 100° C. for 3 minutes, then a gradient from 100° C. to 325° C. over 5.63 minutes. Temperature was held at 325° C. for 3.38 minutes for a final run time of 12.0 minutes.

Reaction rate of esterification was defined as micromoles octyl octanamide produced over time. The slope of each initial amidation rate (defined as reaction velocity) was divided by mg dry resin with immobilized lipase to yield a specific activity: micromoles octyl octanamide minute$^{-1}$ gram resin$^{-1}$. The initial synthesis rate of WT lipase and variant 554 is 1.9 times greater than the WT lipase activity.

| Micromoles octyl octanamide minute$^{-1}$ gram resin$^{-1}$ | | | |
|---|---|---|---|
| n = 2 | Empty vector | WT | 554 |
| Avg | 1.4 | 38.5 | 73.5 |
| Ratio to WT | | 1.0 | 1.9 |

Example 10

Random Mutations Combine to Improve Synthesis Activity in 554 Background

Four additional amino acid substitutions were identified following random mutagenesis and screening and were combined in the 554 background to further improve synthesis activity. Changes A141T, A146T, I189V, V235A were identified by random mutagenesis using the screening protocol described in Example 3. These changes appeared to increase CALB synthesis activity independently and to different degrees in different backgrounds. The systematic combination of random changes in the 554 background (E188D, D223G, S227T) resulted in eight variants with a range of activities (variants 857, 984, 940, 880, 959, 965, 953, and 963). Variant 963 with all 7 amino acid changes shows the highest benzoic acid esterification activity.

| Variant | Average Benzoate Synthesis Activity (n = 4) | A141 | A146 | E188 | I189 | D223 | S227 | V235 |
|---|---|---|---|---|---|---|---|---|
| 857 | 7.2 | T | | D | | G | T | |
| 984 | 7.3 | T | T | D | | G | T | |

-continued

| Variant | Average Benzoate Synthesis Activity (n = 4) | A141 | A146 | E188 | I189 | D223 | S227 | V235 |
|---|---|---|---|---|---|---|---|---|
| 940 | 8.4 | T | | D | V | G | T | |
| 880 | 7.8 | T | | D | | G | T | A |
| 959 | 8.5 | T | T | D | | G | T | A |
| 965 | 9.8 | T | T | D | V | G | T | |
| 953 | 10.0 | T | | D | V | G | T | A |
| 963 | 11.9 | T | T | D | V | G | T | A |

Random mutagenesis: The template for mutagenic PCR was a WT CALB or variant coding region cloned into the modified pHT43Δ vector. Vector primers 2619_F and 2990_R were used as primers. Taq DNA polymerase (NEB). The Taq polymerase buffer was supplemented with an additional 2.5 mM MgCl2 and 0.1 mM MnSO4 to promote nucleotide changes in the coding region. The pHT43Δ vector fragment (with the laqI deletion for constitutive expression) was amplified with primers (SIGSEQ_R and G341_F) using a high-fidelity polymerase blend (LongAmp Taq, NEB), then the vector and mutagenized insert fragments were combined in a multimerization reaction (LongAmp Taq, no added primers), in which the overlapping ends of the vector and insert fragments served to prime the extension reaction, creating long linear repeats of alternating insert and vector. These were used to transform *B. subtilis* strain WB800N directly. Colonies expressing an active lipase were selected for screening at 2 ml scale, and the insert from high-activity leads was sequenced to determine the resulting amino acid sequence.

Benzoic acid esterification activity (BZA): *Bacillus subtilis* WB800N was transformed with the CALB variant expression constructs corresponding to variants 857, 984, 940, 880, 959, 965, 953, and 963. Four separate colonies were picked into expression media for each variant, and expressed at 25 ml scale and immobilized as described in Example 3. The standard benzoic acid (BZA) synthesis screening reaction results were determined for the 4 independent transformants, and the average activity is reported in the Table above.

| | Primer sequences, 5' to 3' |
|---|---|
| 2619_F | GCTTGGTACCAGCTATTGTAACATAATCG (SEQ ID NO: 23) |
| 2990_R | CAGACAAAGATCTCCATGGACGCGTG (SEQ ID NO: 24) |
| G341_F | GGTAAGAGAACTTGTTCTGGTATTGTTACTCCATAATA ACCC (SEQ ID NO: 25) |
| SIGSEQ_R | CAGCGTGCACATAAGCACAAGTCTGAACGAAACTGTCC GC (SEQ ID NO: 26) |

Example 11

Octyl Octanoate Synthesis Kinetics of Variants 857, 984, 940, 880, 959, 965, 953, and 963

CALB variants 857, 984, 940, 880, 959, 965, 953, and 963 were expressed in *Bacillus subtilis* as described in Example 3, and the secreted lipase was adsorbed from the broth onto Purolite ECR1030M resin. The dried resin was used in synthesis reactions to compare the octyl octanoate synthesis activities of the different lipase sequences as described in Example 7.

The following were added to a 3 dram glass vial: stir bar, 0.46 grams (3.5 mmoles) 1-octanol and 0.5 grams (3.5 mmoles) octanoic acid. The reaction was prepared in triplicate, and run and analyzed as in Example 7.

Reactions were initiated by adding carefully pre-weighed dry resin with immobilized lipase (~30 mg each) into each reaction vial. Upon addition of lipase to each vial a stopwatch was immediately started. Vials were staggered in 30 second intervals to allow for consistent sampling. 50 µl was transferred from each vial to pre-weighed GC vials every 10 minutes for a total of 60 minutes for each reaction vial.

GC vials with added sample were then weighed and individual sample weights utilized to calculate micromoles octyl octanoate produced at each time point. A calibration curve was generated prior to reaction sampling using 2 mg/ml 1-methylnaphthalene in toluene as an internal standard. A calibration curve for octyl octanoate demonstrated linear response on the GC in the concentration range of 1.0 to 40.0 mg/ml octyl octanoate.

GC analysis: to each GC vial containing the above 50 µl sample was added 500 µl 2 mg/ml 1-methylnaphthalene (in toluene) as internal standard and 1000 µl toluene. Vials were capped and mixed by inversion. Each vial was analyzed on an Agilent 6890 gas chromatograph equipped with a 5% diphenyl/95% dimethyl polysiloxane capillary (20 m length, 0.25 mm ID, 0.25 µm film thickness, Restek RTX-5 Cat #10223-124) GC column and a flame ionization detector. Initial temperature was held at 100° C. for 3 minutes, then a gradient from 100° C. to 325° C. over 5.63 minutes. Temperature was held at 325° C. for 2.38 minutes for a final run time of 11.0 minutes.

Reaction rate of esterification was defined as micromoles octyl octanoate produced over time. The slope of each initial esterification rate (defined as reaction velocity) was divided by mg dry resin with immobilized lipase to yield a specific activity: micromoles octyl octanoate minute$^{-1}$ gram resin$^{-1}$. The initial synthesis rate of lipase variants 857, 984, 940, 880, 959, 965, 953, and 963 is 3.4 to 9.4 times greater than the WT lipase activity.

| | Micromoles octyl octanoate minute$^{-1}$ gram resin$^{-1}$ | | | | | | | | |
|---|---|---|---|---|---|---|---|---|---|
| 1:1 octanol:acid | WT | 857 | 984 | 940 | 880 | 959 | 965 | 953 | 963 |
| Avg (st dev) | 84.2 (6) | 364 (15) | 320 (9) | 370 (22) | 405 (1) | 441 (24) | 532 (47) | 526 (19) | 645 (4) |
| Ratio to WT | 1.0 | 4.3 | 3.8 | 4.4 | 4.8 | 5.2 | 6.3 | 6.2 | 7.7 |

Example 12

2-ethylhexyl Palmitate Synthesis Kinetics of Variants 857, 984, 940, 880, 959, 965, 953, and 963

The 2-EHP assay was performed as described in Example 8. In a 50 ml conical tube, 50 mg of dry resin with immobilized lipase and 10 grams of Palmitic Acid were weighed into each tube, 1.03 equivalents (5.23 grams) of 2-Ethylhexanol was added. The tube was heated in 72° C. water bath for 45 minutes to melt all starting materials. Once melted each tube was placed in a heat block set at 72° C. A sparge needle was inserted into each tube through a vented cap to mix and nitrogen-strip the reaction. The sparge rate was set to 300 mL/min dry nitrogen for each tube.

Samples were taken at 0, 1 h, 2 h, 4 h, and 24 h and accurately weighed for analysis by a wt % GC method. GC analysis: Analyzed on a Hewlett-Packard 5890 GC equipped with a J&W DB-5 column, 30 m×0.25 mm with flame ionization detection and split injection with 2 uL injection volume. Temperature program: 100° C. for 9 min, then 100-300° C. at a rate of 25° C./min, hold at 300° C. for 10 min.

The initial rate of conversion (% palmitic acid converted/h) was determined from the slope of the data points from 0 to 4 h. The conversion rate relative to WT is also reported. Lipase variants with 4 to 7 amino acid changes have a 2-ethylhexyl palmitate synthesis rate 2 to 3-fold greater than WT CALB.

| | WT | 857 | 984 | 940 | 880 | 959 | 965 | 953 | 963 |
|---|---|---|---|---|---|---|---|---|---|
| wt % palmitic acid converted to ester (h−1) | 0.72 | 1.82 | 1.46 | 1.87 | 1.63 | 2.09 | 1.84 | 1.84 | 2.22 |
| Ratio to WT | 1.0 | 2.5 | 2.0 | 2.6 | 2.3 | 2.9 | 2.6 | 2.6 | 3.1 |

Example 13

Octyl Methacrylate Synthesis Kinetics of WT and Variants 554, 857 and 963

WT CALB and variants 554, 857, and 963 were expressed in *Bacillus subtilis* as described in Example 3, and the secreted lipase was adsorbed from the broth onto Purolite™ ECR1030M resin. The dried resin was used in synthesis reactions to compare the octyl methacrylate synthesis activities of the different lipase variants.

An equimolar mix of octanol and methyl methacrylate was prepared, and each variant was analyzed in triplicate. The following were added to a 3 dram glass vial: stir bar, 0.5 grams mix. Reactions were initiated by adding carefully pre-weighed dry resin with immobilized lipase (~50 mg) into each reaction vial. Upon addition of lipase to each vial a stopwatch was immediately started. Vials were staggered in 30 second intervals to allow for consistent sampling. Ten microliters was transferred from each reaction vial to 0.5 ml methanol in GC vials every 60 minutes for a total of 360 minutes for each reaction.

Each sample was analyzed on an Agilent 6890 gas chromatograph equipped with a 5% diphenyl/95% dimethyl polysiloxane capillary (20 m length, 0.25 mm ID, 0.25 μm film thickness, Restek RTX-5 Cat #10223-124) GC column and a flame ionization detector. Initial temperature was held at 100° C. for 3 minutes, then a gradient from 100° C. to 325° C. over 5.63 minutes. Temperature was held at 325° C. for 2.38 minutes for a final run time of 11.0 minutes. The octanol and octyl methacrylate peaks were integrated, and reaction rate of esterification was estimated as peak area % octyl methacrylate produced over time based on dry resin weight. The initial synthesis rate of lipase variants 554, 857, and 963 are 2.8 to 5 times greater than the WT lipase activity.

| Relative octyl methacrylate hour$^{-1}$ gram resin$^{-1}$ | | | | |
|---|---|---|---|---|
| 1:1 octanol:acid | WT | 554 | 857 | 963 |
| Avg (n = 3) | 4.8 | 13.2 | 16.8 | 24.0 |
| Ratio to WT | 1.0 | 2.8 | 3.4 | 5.0 |

The subject matter described above is provided by way of illustration only and should not be construed as limiting. Various modifications and changes may be made to the subject matter described herein without following the example embodiments and applications illustrated and described, and without departing from the true spirit and scope of the present invention, which is set forth in the following claims.

All publications, patents and patent applications cited in this specification are incorporated herein by reference in their entireties as if each individual publication, patent or patent application were specifically and individually indicated to be incorporated by reference. While the foregoing has been described in terms of various embodiments, the skilled artisan will appreciate that various modifications, substitutions, omissions, and changes may be made without departing from the spirit thereof.

The invention claimed is:

1. A *Candida antarctica* lipase B (CALB) variant having about two fold to about fifteen fold improved synthesis activity as compared to a wild type (WT) CALB comprising an amino acid sequence of SEQ ID NO: 2, wherein the CALB variant comprises an amino acid sequence that differs from SEQ ID NO: 2 by two to ten amino acid modifications, wherein the two amino acid modifications are at positions 223 and 227 of SEQ ID NO: 2, and wherein the synthesis activity comprises synthesis of an ester or an amide.

2. The CALB variant of claim 1, wherein the CALB variant further comprises an amino acid modification at position 141, 146, 188, 189, or 235 of SEQ ID NO: 2.

3. The CALB variant of claim 1, wherein the amino acid sequence of the CALB variant comprises at least three modifications.

4. The CALB variant of claim 3, wherein the modifications are amino acid substitutions.

5. The CALB variant of claim 4, wherein the amino acid substitutions are A141T, A146T, E188D, I189V, D223G, S227T, or V235A.

6. The CALB variant of claim 5, wherein the CALB variant comprises an amino acid sequence of SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20 or SEQ ID NO: 22.

7. A method of catalyzing synthesis of a carboxylic acid ester, wherein one or more alcohols and one or more carboxylic acids or one or more carboxylic esters are reacted in the presence of the CALB variant of claim 1 to form a carboxylic acid ester.

8. The method of claim 7, wherein at least one of the carboxylic acids is a branched carboxylic acid, or wherein at least one of the carboxylic acid esters is a branched carboxylic acid ester.

9. A method of catalyzing synthesis of an amide, wherein one or more carboxylic acids or carboxylic acid esters and one or more amines are reacted in the presence of the CALB variant of claim 1 to form an amide.

10. The method of claim 9, wherein at least one of the carboxylic acids is a branched carboxylic acid or wherein at least one of the carboxylic acid esters is a branched carboxylic acid ester.

11. A fusion protein comprising the CALB variant of claim 1 and a heterologous peptide.

12. The fusion protein of claim 11, wherein the heterologous peptide is a signal peptide.

* * * * *